(12) United States Patent
Chen et al.

(10) Patent No.: US 12,161,691 B2
(45) Date of Patent: Dec. 10, 2024

(54) PROTEIN INHIBITORS OF CLOSTRIDIUM DIFFICILE TOXIN B

(71) Applicants: The Texas A&M University System, College Station, TX (US); University of Maryland, Baltimore, Baltimore, MD (US)

(72) Inventors: Zhilei Chen, College Station, TX (US); Rudo Simeon, Bryan, TX (US); Ana M. Chamoun-Emanuelli, College Station, TX (US); Zeyu Peng, Kunming (CN); Hanping Feng, Baltimore, MD (US); Hua Yu, Columbia, MD (US); Yongrong Zhang, Columbia, MD (US)

(73) Assignees: The Texas A&M University System, College Station, TX (US); University of Maryland, Baltimore, Baltimore, MD (US)

( * ) Notice: Subject to any disclaimer, the term of this patent is extended or adjusted under 35 U.S.C. 154(b) by 20 days.

(21) Appl. No.: 17/609,818

(22) PCT Filed: May 11, 2020

(86) PCT No.: PCT/US2020/032353
§ 371 (c)(1),
(2) Date: Nov. 9, 2021

(87) PCT Pub. No.: WO2020/231930
PCT Pub. Date: Nov. 19, 2020

(65) Prior Publication Data
US 2022/0226430 A1   Jul. 21, 2022

Related U.S. Application Data

(60) Provisional application No. 62/900,855, filed on Sep. 16, 2019, provisional application No. 62/846,650, filed on May 11, 2019.

(51) Int. Cl.
*A61K 38/16*   (2006.01)
*A61P 39/02*   (2006.01)

(52) U.S. Cl.
CPC ............ *A61K 38/164* (2013.01); *A61P 39/02* (2018.01)

(58) Field of Classification Search
CPC .............................. A61K 38/164; A61P 39/02
See application file for complete search history.

(56) References Cited

U.S. PATENT DOCUMENTS

| | | |
|---|---|---|
| 2004/0106564 A1 | 6/2004 | Nilius |
| 2005/0287150 A1 | 12/2005 | Ambrosino et al. |
| 2015/0030596 A1 | 1/2015 | Cheong et al. |
| 2015/0307563 A1 | 10/2015 | Anderson et al. |
| 2015/0329847 A1 | 11/2015 | Lee et al. |
| 2016/0045591 A1 | 2/2016 | Campos-Neto et al. |
| 2016/0319037 A1 | 11/2016 | Shone et al. |

FOREIGN PATENT DOCUMENTS

| | | |
|---|---|---|
| WO | WO-2011054519 A1 | 5/2011 |
| WO | WO-2016073562 A1 | 5/2016 |

OTHER PUBLICATIONS

Pluckthun, Designed Ankyrin Repeat Proteins (DARPins): Binding Proteins for Research, Diagnostics, and Therapy, Annu. Rev. Pharmacol. Toxicol., 2015, 55, pp. 489-511.*
Clostridioides difficile Infection-CDC, from https://www.cdc.gov/hai/organisms/cdiff/cdiff_infect.html, 2019, p. 1.*
Clostridioides difficile Infection, from https://my.clevelandclinic.org/health/diseases/15548-c-diff-infection, 2023, pp. 1-19.*

* cited by examiner

*Primary Examiner* — Li N Komatsu
(74) *Attorney, Agent, or Firm* — Winstead PC

(57) ABSTRACT

In an embodiment, the present disclosure pertains to a method of treating or preventing *C. difficile* infections. In some embodiments, the method includes administering an antitoxin to a subject in need thereof. In some embodiments, the antitoxin includes a designed ankyrin repeat protein (DARPin). In an additional embodiments, the present disclosure pertains to a composition including an antitoxin for treating or preventing *C. difficile* infections. In some embodiments, the anti-toxin includes a DARPin. In some embodiments, the anti-toxin is a monomeric or dimeric DARPin for the neutralization of *Clostridium difficile* toxin B (TcdB).

13 Claims, 14 Drawing Sheets
Specification includes a Sequence Listing.

| DARPin | EC$_{50}$ (nM) | DARPin | EC$_{50}$ (nM) |
|---|---|---|---|
| 1.2E | 2.4±0.5 | 7.5A | 10.2±3.1 |
| 1.4E | 3±0.7 | 5.9C | 10.2±0.9 |
| 1.8H | 9.1±3.3 | 3.11H | 23.5±12.4 |
| 1.11E | 7.5±1.2 | 3.5B | 13.3±6.9 |
| 5.8B | 10.4±2.3 | 8.1B | 14.4±6.6 |
| 5.5A | 11.3±3.0 | 3.9G | 42.7±21.2 |

| DARPin dimer | N-DARPin | C-DARPin | EC$_{50}$ (nM) |
|---|---|---|---|
| DLD-1 | 5.5A | 7.5A | 0.43 ±0.375 |
| DLD-2 | 1.8H | 1.2E | 1.04 ±0.594 |
| DLD-3 | U3 | 5.9C | 0.0515±0.054 |
| DLD-4 | U3 | 1.4E | 0.004 ± 0.001 |
| DLD-5 | U5 | 5.8B | 0.031 ± 0.013 |
| DLD-6 | U3 | 3.5B | 0.0125± 0.011 |
| DLD-7 | U3 | 5.5A | 0.014 ± 0.014 |
| DLD-10 | U3 | 5.8B | 0.005 ± 0.001 |
| DLD-11 | U3 | 1.2E | 0.290 ± 0.109 |
| DLD-12 | U3 | 1.11E | 0.008 ± 0.005 |

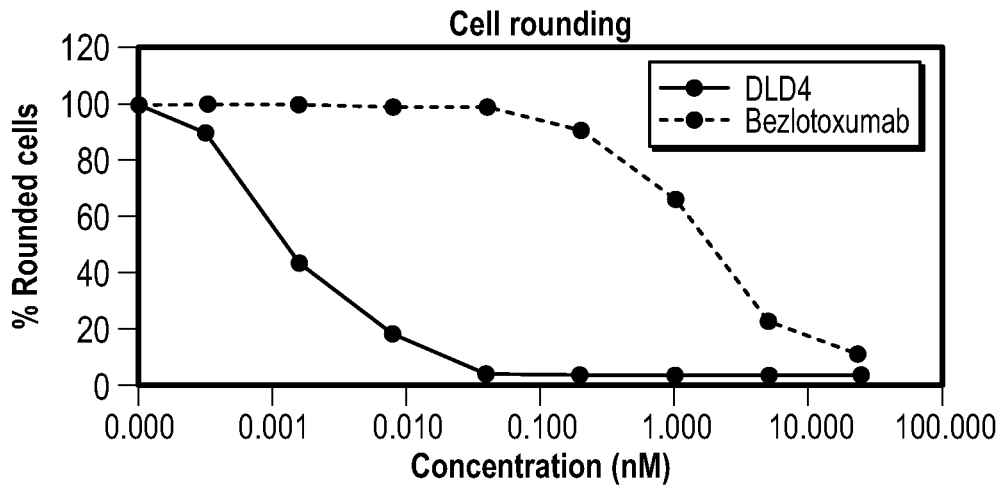
FIG. 7A
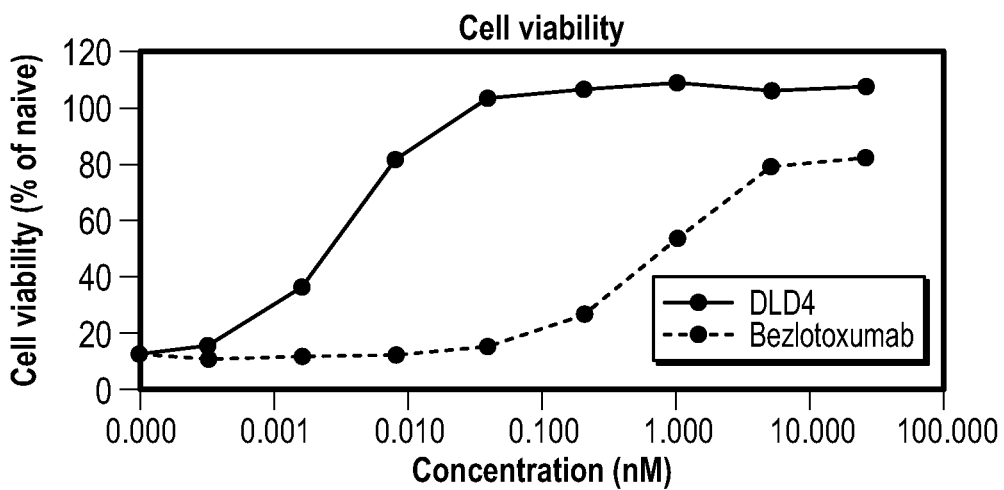
FIG. 7B
| Sample | EC$_{50}$ (nM) | |
|---|---|---|
| | Cell rounding | Cell viability |
| DLD4 | 0.002 | 0.005 |
| Bezlotoxumab | 1.508 | 0.707 |
FIG. 7C

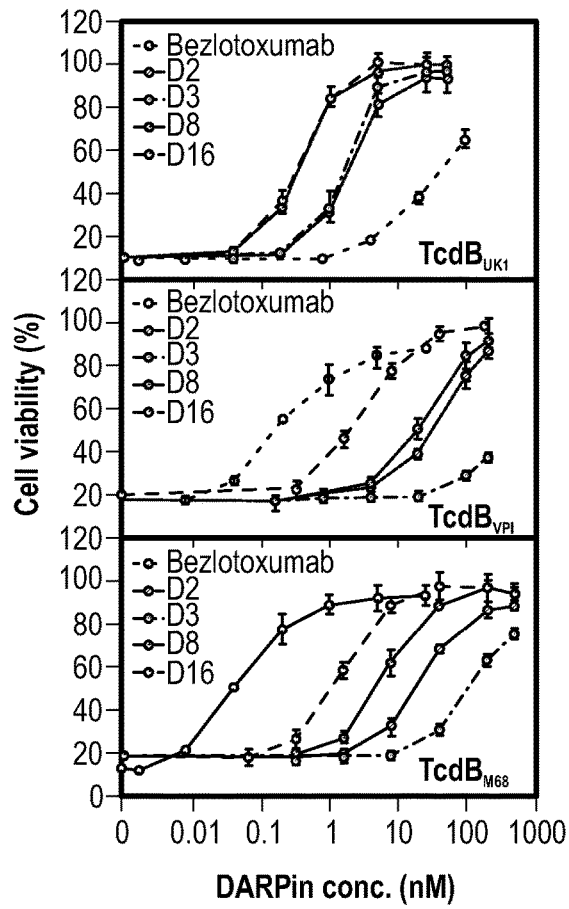
FIG. 8A
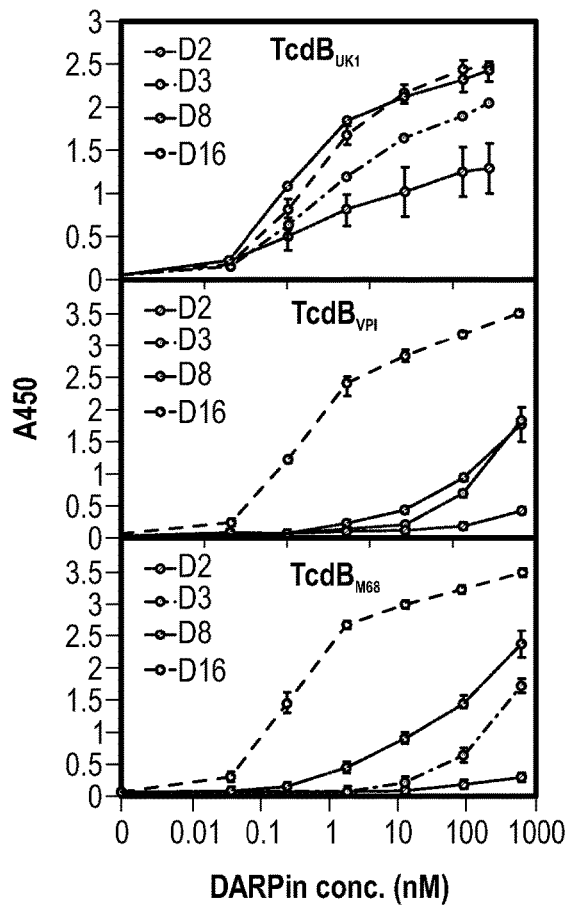
FIG. 8B
| Anti-toxin | EC$_{50}$(nM) | | |
|---|---|---|---|
| | UK1 | VPI | M68 |
| D2 | 3.04±0.28 | >20 | 26.64±3.53 |
| D3 | 2.43±0.20 | >200 | >40 |
| D8 | 0.60±0.05 | ~20 | 7.78±0.51 |
| D16 | 0.50±0.03 | 5.20±0.79 | 1.62±0.13 |
| Bezlotoxumab | ~33 | 0.61±0.08 | 0.10±0.01 |
FIG. 8C

PROTEIN INHIBITORS OF CLOSTRIDIUM DIFFICILE TOXIN B

CROSS-REFERENCE TO RELATED APPLICATIONS

This patent application claims priority from, and incorporates by reference the entire disclosure of, U.S. Provisional Application No. 62/846,650 filed on May 11, 2019 and U.S. Provisional Application No. 62/900,855 filed on Sep. 16, 2019.

STATEMENT REGARDING FEDERALLY SPONSORED RESEARCH OR DEVELOPMENT

This invention was made with government support under R21AI126025 awarded by the National Institutes of Health. The government has certain rights in the invention.

TECHNICAL FIELD

The present disclosure relates generally to *Clostridium difficile* toxin B and more particularly, but not by way of limitation, to compositions and methods of use for protein inhibitors of *Clostridium difficile* toxin B.

BACKGROUND

*Clostridium difficile* infection (CDI) is a major nosocomial disease associated with significant morbidity and mortality. The pathology of CDI stems primarily from the two *C. difficile* secreted exotoxins—toxin A (TcdA) and toxin B (TcdB)—that disrupt the tight junctions between epithelial cells leading to the loss of colonic epithelial barrier function. The present disclosure reports the engineering of a series of monomeric and dimeric Designed Ankyrin Repeat Proteins (DARPins) for the neutralization of TcdB.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, a method of treating or preventing *C. difficile* infections, where the method includes administering an anti-toxin to a subject in need thereof, where the anti-toxin includes a designed ankyrin repeat protein (DARPin). In some embodiments, the anti-toxin includes at least one of the proteins U3 (SEQ ID NO. 13) and 1.4E (SEQ ID NO. 02). In some embodiments, the anti-toxin binds to a region on TcdA, TcdB, or combinations thereof that is critical for toxin translocation into host cytosol. In some embodiments, the anti-toxin includes one of proteins DLD-4 (SEQ ID NO. 37), DLD-1 (SEQ ID NO. 34), DLD-2 (SEQ ID NO. 35), DLD-3 (SEQ ID NO. 36), DLD-5 (SEQ ID NO. 38), DLD-6 (SEQ ID NO. 39), DLD-7 (SEQ ID NO. 40), DLD-10 (SEQ ID NO. 41), DLD-II (SEQ ID NO. 42), DLD-12 (SEQ ID NO. 43), or combinations thereof. In some embodiments, the anti-toxin includes one of proteins 1.4E (SEQ ID NO. 02), 1.2E (SEQ ID NO. 01), 1.8H (SEQ ID NO. 03), 1.11E (SEQ ID NO. 04), 5.8B (SEQ ID NO. 05), 5.5A (SEQ ID NO. 06), 7.5A (SEQ ID NO. 07), 5.9C (SEQ ID NO. 08), 3.11H (SEQ ID NO. 09), 3.5B (SEQ ID NO. 10), 8.1B (SEQ ID NO. 11), 3.9G (SEQ ID NO. 12), U3 (SEQ ID NO. 13), U5 (SEQ ID NO. 14), or combinations thereof.

In another embodiment, a composition including an anti-toxin for treating or preventing *C. difficile* infections, where the anti-toxin includes a designed ankyrin repeat protein (DARPin). In some embodiments, the anti-toxin includes at least one of U3 (SEQ ID NO. 13) and 1.4E (SEQ ID NO. 02), and the anti-toxin binds to a region on TcdA, TcdB, or combinations thereof that is critical for toxin translocation into host cytosol. In some embodiments, the anti-toxin includes DLD-4 (SEQ ID NO. 37), DLD-1 (SEQ ID NO. 34), DLD-2 (SEQ ID NO. 35), DLD-3 (SEQ ID NO. 36), DLD-5 (SEQ ID NO. 38), DLD-6 (SEQ ID NO. 39), DLD-7 (SEQ ID NO. 40), DLD-10 (SEQ ID NO. 41), DLD-11 (SEQ ID NO. 42), DLD-12 (SEQ ID NO. 43), or combinations thereof. In some embodiments, the anti-toxin includes 1.4E (SEQ ID NO. 02), 1.2E (SEQ ID NO. 01), 1.8H (SEQ ID NO. 03), 1.11E (SEQ ID NO. 04), 5.8B (SEQ ID NO. 05), 5.5A (SEQ ID NO. 06), 7.5A (SEQ ID NO. 07), 5.9C (SEQ ID NO. 08), 3.11H (SEQ ID NO. 09), 3.5B (SEQ ID NO. 10), 8.1B (SEQ ID NO. 11), 3.9G (SEQ ID NO. 12), U3 (SEQ ID NO. 13), U5 (SEQ ID NO. 14), or combinations thereof.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 7A, FIG. 7B, and FIG. 7C illustrate DARPins dimers offer superior inhibition of TcdB from *C. difficile* strain VPI 10463 (ribotype 087).

FIG. 8A and FIG. 8B show that DARPins strongly exhibit the ability to neutralize (A) and bind (B) the different TcdB toxins. FIG. 8C shows TcdB neutralization potency of different DARPins and bezlotoxumab.

DETAILED DESCRIPTION

Figure 1A:
FIG. 1A shows a monomeric designed ankyrin repeat protein (DARPin) sequence in schematic form.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

*Clostridium difficile* is a gram-positive spore-forming anaerobic bacterium. Colonization of the gut with pathogenic *C. difficile* can lead to *C. difficile* infection (CDI) with symptoms including diarrhea, pseudomembranous colitis, sepsis, multiple organ dysfunction syndrome and even death. In 2011 there were almost half a million reported cases of CDI and more than 29,000 CDI-associated deaths in the United States alone. *C. difficile* is considered a major nosocomial pathogen as a significant percentage (7%) patients acquire CDI after hospitalization. Broad-spectrum antibiotics are considered a major culprit of CDI, as they disrupt the patients' natural gut microflora that would otherwise keep the proliferation of *C. difficile* in check. The current standard-of-care for treating CDI is the administration of additional antibiotics, mainly vancomycin, metronidazole and fidaxomicin. Although this approach is generally effective against primary CDI, in recent decades, the rate of CDI recurrence has significantly increased due to the emergence of antibiotic-resistant and so-called hypervirulent strains (15-35% CDI recurrence in patients after cessation of antibiotic treatment).

CDI is the leading cause of hospital-acquired infectious diarrhea, claiming the lives of ~30,000 people each year and >$6 billion in treatment-associated costs. The symptoms of CDI range from mild cases of diarrhea to fatal pseudomembranous colitis. Although primary CDI can generally be treated with antibiotics, over the past decades, the rate of CDI recurrence has greatly increased due to the emergence of antibiotic-resistant and so-called hyper-virulent strains many patients (20-25% relapses). *C. difficile* secreted toxins A (TcdA) and toxin B (TcdB) are the critical virulence factors that cause diseases associated with CDI. The pathology of CDI mainly stems from the two *C. difficile* secreted exotoxins, toxin A (TcdA) and toxin B (TcdB), that target small GTPases within the host cells, leading to 20 disruption of the tight junctions and loss of colonic epithelial barrier function. The anti-TcdB monoclonal antibody bezlotoxumab (ZINPLAVA™) was approved by the FDA in 2016 for treating recurrent CDI. The CDI recurrence rate in patients receiving antibiotics together with i.v. infusion of bezlotoxumab, although lower than those receiving antibiotics alone (26-28%), remains high at 15-17%.

Recently, ZINPLAVA™ (bezlotoxumab, an intravenously administered anti-TcdB monoclonal antibody to be used concurrent with antibiotics) was approved by the FDA for treating recurrent CDI. The market value of ZINPLAVA™ is predicted to reach over US$212 million by 2020. However, even with ZINPLAVA™, the rate of recurrence remains high at 15-17%. Thus, more effective therapy against CDI is still urgently needed.

Embodiments of the claimed invention are directed to the engineering of a panel of DARPins as potent anti-toxins against TcdB. DARPin is a small non-antibody binding scaffold protein that exhibits very high thermostability, resistance to proteases and denaturants, and very low immunogenicity. Unlike antibody that needs to be expressed in mammalian cells and is expensive to produce, DARPins can be expressed at very high levels in *E. coli* (multi-gram quantities per liter of culture in fermenters), enabling DARPins to be produced at low cost on a large scale. Using phage panning combined with high-throughput in vitro functional screening, several DARPins with picomolar neutralization potency against TcdB were engineered. One of the identified DARPins in accordance with embodiments of the disclosure, DLD-4 (SEQ ID NO. 37), inhibited TcdB with $EC_{50}$ of 4 pM in vitro, which is >300-fold more potent than ZINPLAVA™.

The anti-toxin DARPins of the claimed invention can potentially replace ZINPLAVA™ for the treatment of CDI. Since DARPins can be made at a fraction of the cost of ZINPLAVA™ (due to the different expression platform), antitoxin DARPins will have a significant price advantage over ZINPLAVA™ (currently at ~US $3,000/dose). Additionally, due to the high stability and ease of production, anti-toxin DARPins can potentially be formulated as oral therapeutics to directly neutralize the toxin in the gut. Since *C. difficile* and its secreted toxins reside in the gastrointestinal (GI) tract, a location not easily accessible by i.v. administered antibody, it is believed that an oral toxin-neutralizer should be more effective at preventing CDI pathogenesis.

As such, a goal of the present disclosure is to develop highly efficacious anti-toxin proteins as oral therapeutics that can directly neutralize the toxins in the gut for treating and/or preventing the recurrent of CDI. These anti-toxin proteins are based on a designed ankyrin repeat protein (DARPin), a small antibody-mimic binding scaffold that exhibits very high thermostability, resistance to proteases and denaturants, and a very low immunogenicity. DARPins that bind a wide range of molecules with pico- to nano-molar affinity have been identified. Furthermore, DARPins can be expressed at high levels in *E. coli* (multi-gram quantities per liter of culture in fermenters), enabling DARPins to be produced at potentially very low cost on a large scale.

Combining phage panning and functional screening, a panel of dimeric DARPins with picomolar in vitro TcdB neutralization potency were identified. An identified DARPin in accordance with an embodiment of the claimed invention, DLD-4 (SEQ ID NO. 37), exhibited an $EC_{50}$ of 4 pM and 20 pM against TcdB from *C. difficile* strains VPI10463 (ribotype 087) and M68 (ribotype 120), respectively, which is ~330-fold and ~33-fold more potent than the FDA-approved anti-TcdB monoclonal antibody bezlotoxumab. DARPin DLD-4 (SEQ ID NO. 37) was also efficacious in vivo in two mouse models against TcdB challenge, pointing to its potential as a next-generation anti-toxin biologic for treating CDI and/or preventing its recurrence.

In view of the aforementioned, an aspect of the present disclosure relates generally to the treatment and prevention of *C. difficile* infections. In some embodiments, the toxin-neutralizing DARPins disclosed herein are easy to express and relatively resistance to environmental stress thus potentially delivered to intestines to block toxins' actions. In some embodiments, anti-toxin DARPin can be used in different types of products, such as, for example, anti-toxin DARPin solution to be administered intravenously, similar to that of ZINPLAVA™, anti-toxin DARPin to be formulated in capsule or pills and be administered orally to directly neutralize the toxins in the GI tract, anti-toxin DARPins to be secreted by engineered commensal bacteria (e.g. *Lactococcus lactis, lactobacillus*) or commensal yeast (e.g. *Saccharomyces boulardii*) to provide in situ delivery of toxin neutralizer in the gut, or combination thereof.

Additional embodiment of the present disclosure pertain to methods of treating or preventing *C. difficile* infections. In some embodiments, the method includes administering an anti-toxin to a subject in need thereof, where the anti-toxin includes a DARPin. In some embodiments, the DARPin neutralizes a *C. difficile* secreted exotoxins. In some embodiments, the *C. difficile* secreted exotoxin is TcdB. In some embodiments, the anti-toxin includes compositions comprising at least one of U3 (SEQ ID NO. 13), D2 (SEQ ID NO. 27), D3 (SEQ ID NO. 16), D8 (SEQ ID NO. 24), D16 (SEQ ID NO. 23), and combinations thereof. In some embodiments, the anti-toxin includes U3 (SEQ ID NO. 13) and D16 (SEQ ID NO. 23). In some embodiments, the anti-toxin neutralizes TcdB by blocking its interaction with the receptor chondroitin sulfate proteoglycan 4 (CSPG4). In some embodiments, the anti-toxin is adapted to be administered intravenously. In some embodiments, the anti-toxin is adapted to be administered orally. In some embodiments, the anti-toxin is adapted to be administered in situ. In some embodiments, the anti-toxin is a dimeric DARPin U3D16 (SEQ ID NO. 49) which pairs DARPin D16 (SEQ ID NO. 23) with DARPin U3 (SEQ ID NO. 13). In some embodiments, the dimeric DARPin U3D16 (SEQ ID NO. 49) disrupts interaction of TcdB with Frizzled 1/2/7 receptor.

In a further embodiment, the present disclosure pertains to compositions having an anti-toxin for treating or preventing *C. difficile* infections, where the anti-toxin includes a DARPin. In some embodiments, the DARPin neutralizes a *C. difficile* secreted exotoxins. In some embodiments, the *C. difficile* secreted exotoxin is TcdB. In some embodiments, the anti-toxin includes at least one of U3 (SEQ ID NO. 13), D2 (SEQ ID NO. 27), D3 (SEQ ID NO. 16), D8 (SEQ ID NO. 24), D16 (SEQ ID NO. 23), and combinations thereof. In some embodiments, the anti-toxin includes U3 (SEQ ID NO. 13) and D16 (SEQ ID NO. 23). In some embodiments, the anti-toxin neutralizes TcdB by blocking its interaction with the receptor CSPG4. In some embodiments, the anti-toxin is adapted to be administered intravenously. In some embodiments, the anti-toxin is adapted to be administered orally. In some embodiments, the anti-toxin is adapted to be administered in situ. In some embodiments, the anti-toxin is a dimeric DARPin U3D16 (SEQ ID NO. 49) which pairs DARPin D16 (SEQ ID NO. 23) with DARPin U3 (SEQ ID NO. 13). In some embodiments, the dimeric DARPin U3D16 (SEQ ID NO. 49) disrupts interaction of TcdB with Frizzled 1/2/7 receptor. In some embodiments, the anti-toxin is a DARPin monomer. In some embodiments, the anti-toxin is a DARPin dimer.

In some embodiments, the engineering of these ultra-potent TcdB-neutralizing DARPins involves three sequential steps: i) phage-panning of a DARPin library against purified TcdB; ii) functional screening for DARPins with TcdB-neutralization activity; iii) functional screening of dimeric DARPins with enhanced TcdB-neutralization activity. In some embodiments, anti-TcdB DARPin is produced from *E. coli* using standard molecular biology techniques. In some embodiments, large-scale protein expression can be done in a fermenter. In some embodiments, disclosed herein, are ways to improve stability against protease digestion and expand neutralization spectrum against TcdB from different strains of *C. difficile*.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

The present disclosure aims to engineer a highly efficacious microbial-expression compatible antibody surrogate protein, a designed ankyrin repeat protein (DARPin), to neutralize *C. difficile* toxin TcdB. DARPins represent a versatile class of binding proteins that have been engineered to bind diverse targets with up to picomolar affinity. Furthermore, DARPins are also amenable to high-yield production in microbial expression hosts. Given these attractive properties of DARPins, the present disclosure seeks to create DARPin-based oral therapeutics against CDI infection.

The engineering of a panel of DARPins with superior in vitro toxin neutralization potency against *C. difficile* toxin TcdB than the FDA-approved anti-TcdB monoclonal antibody bezlotoxumab is disclosed herein. These highly potent DARPin-based anti-toxins possess the potential to be developed into therapeutics to treat CDI and/or prevent its recurrence. The present disclosure envisions making the molecules from this disclosure amenable to oral administration.

TcdB Expression and Purification

Plasmid DNA encoding a 6-His tagged-TcdB was transformed into *Bacillus megaterium* cells and the recombinant TcdB was purified via Ni-NitriloTriacetic Acid (NTA) affinity column. The column was washed with high-salt PBS (20 mM $NaH_2PO_4$, 20 mM $Na_2HPO_4$, 300 mM NaCl, pH 7.4) containing 25 mM imidazole and the bound protein was eluted using high-salt phosphate-buffered saline (PBS) containing 250 mM imidazole. Eluted protein was diluted in low-salt PBS (20 mM $NaH_2PO_4$, 20 mM $Na_2HPO_4$, 10 mM NaCl, pH 7.4) to obtain a final NaCl concentration of 30 mM and the mixture was loaded onto a Q HP anion exchange column (GE Healthcare). The column was washed with the same low-salt PBS buffer and bound protein was eluted using a salt gradient from 10 mM to 1 M NaCl. TcdB eluted at NaCl concentrations of ~500 mM. Protein purity was confirmed using sodium dodecyl sulfate-polyacrylamide gel electrophoresis (SDS-PAGE).

DARPin Library Creation and Phage Panning

Figure 1B:
FIG. 1B shows a dimeric designed ankyrin repeat protein (DARPin) sequence in schematic form.
Figure 1C:
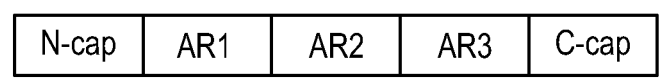
FIG. 1C shows a schematic of a DARPin in accordance with an embodiment of the invention.

FIG. 1A and FIG. 1B illustrate designed ankyrin repeat protein (DARPin) sequences in schematic form. In each DARPin construct there is an N-terminal hexa-His tag followed by a myc tag, shown in FIG. 1A. In the dimeric construct, DARPins are separated by a (GGGGS)×3 (SEQ ID NO. 48) linker sequence, shown in FIG. 1B. FIG. 1C shows a schematic of a DARPin in accordance with an embodiment of the invention. DARPins are composed of repeat modules of natural ankyrin protein and comprise an N-terminal capping repeat (N-cap), three internal, contiguously arranged ankyrin repeats (ARs) and a C-terminal capping repeat (C-cap) as schematically depicted in FIG. 1C. In a DARPin library, each internal repeat contains six randomized positions, yielding a total of 18 randomized positions in each DARPin. Such a DARPin library was prepared using sequential ligation and polymerase chain reaction (PCR). This DARPin library was positioned downstream of a DsbAss cotranslational translocation signal peptide and fused to the N-terminus of the bacteriophage M13 gIII minor coat protein. A DARPin library consisting of $\sim 2 \times 10^9$ unique clones was created by transforming $\sim 12$ mL high-efficiency MC1061 electro-competent cells with $\sim 250$ µg of ligated and purified DNA.

Phage panning was carried out as follows. TcdB (from *C. difficile* VPI10463) was biotinylated via EZ-Link-Sulfo NHS-LC Biotin (Pierce) and used as the target protein. Four rounds of sequential phage panning were performed. The enrichment of TcdB-binding DARPin was confirmed by phage ELISA following a published protocol. A plateau in the level of TcdB binding was observed after round 3 of panning, indicative of successful phage panning.

Figure 4:
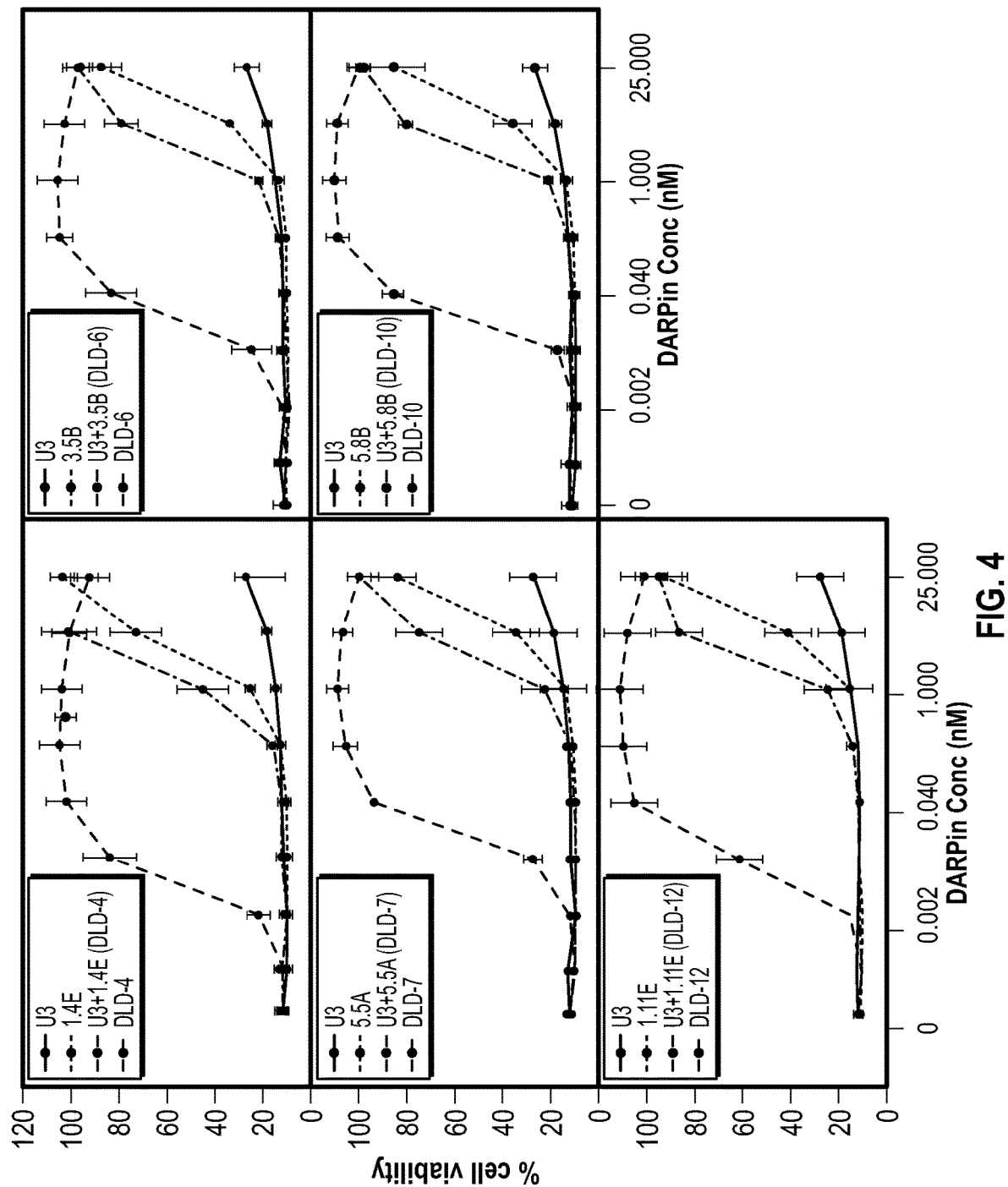
FIG. 4 illustrates DARPin dimers exhibit superior toxin-neutralization potency relative to the constituent monomers.
Figure 6:
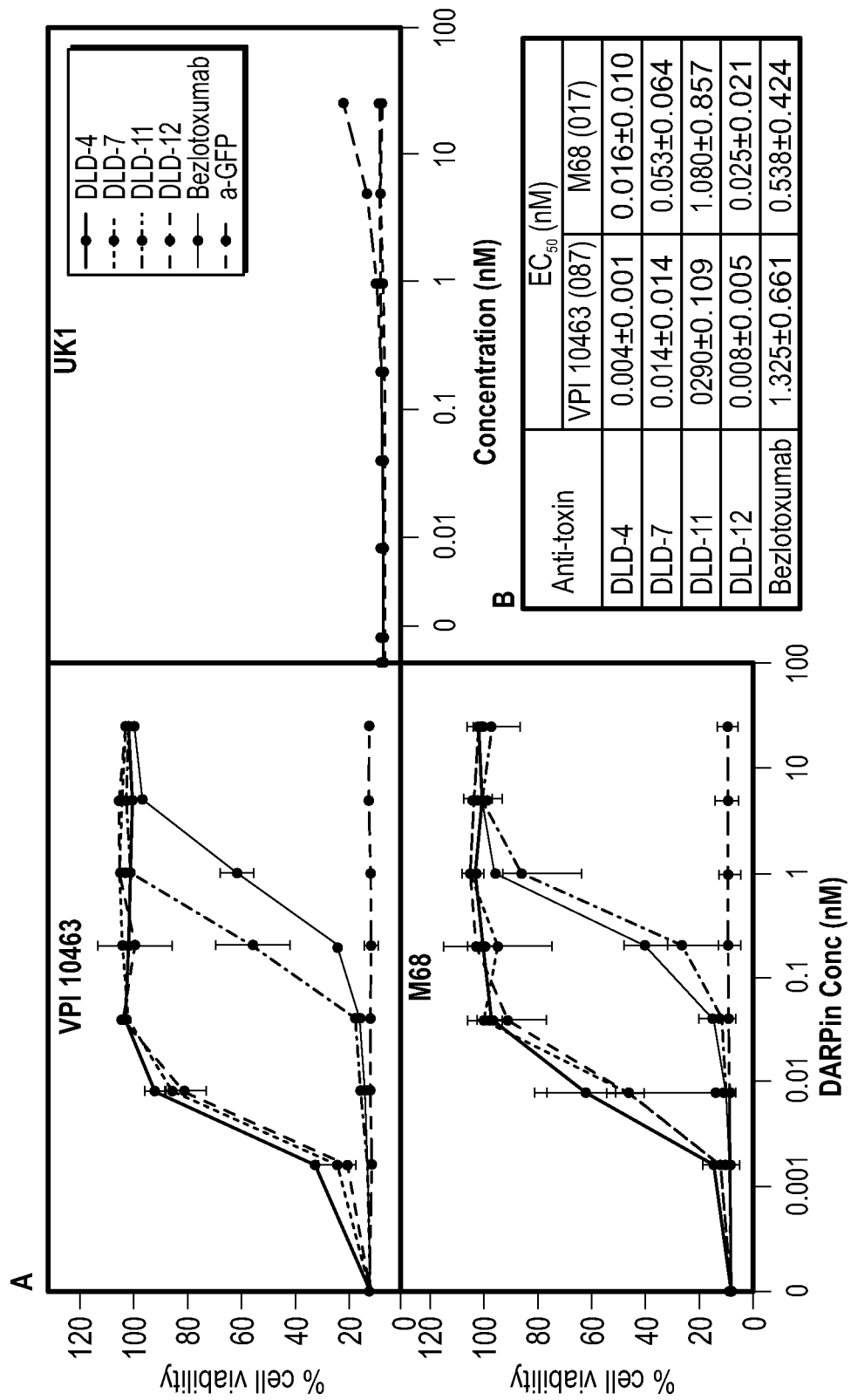
FIG. 6A and FIG. 6B illustrate DARPin dimers offer superior protection to Vero cells against the toxicity of TcdB from *C. difficile* strains VPI 10463 (ribotype 087) and M68 (ribotype 017).
Figure 9B:
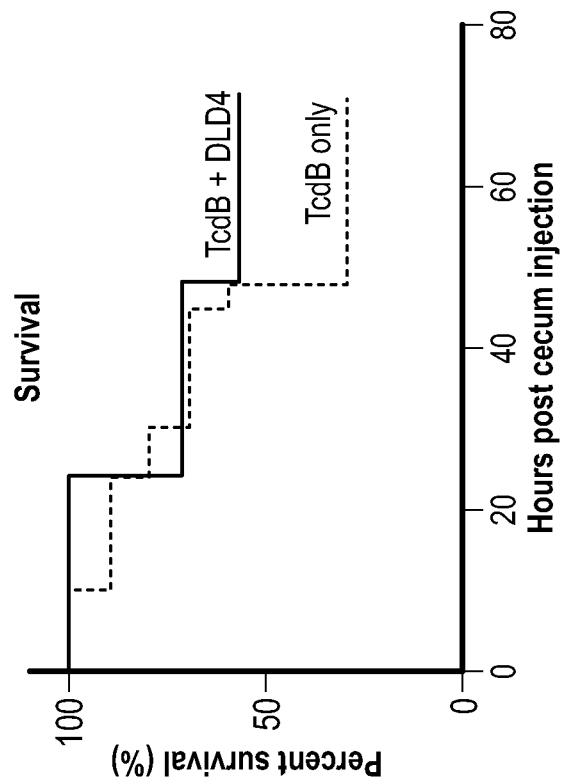
FIG. 9B shows DLD-4 (SEQ ID NO. 37) (5 mg/mouse) was mixed with TcdB (15 µg/mouse) in 100 µL PBS and injected immediately into the cecum of mice (n=7). The control group received the same dose of TcdB alone (n=10). Mouse survival was monitored for 3 days and the data were analyzed by Kaplan-Meier survival analysis. P=0.349 (TcdB only vs. TcdB+DLD-4 (SEQ ID NO. 37)).
Figure 9A:
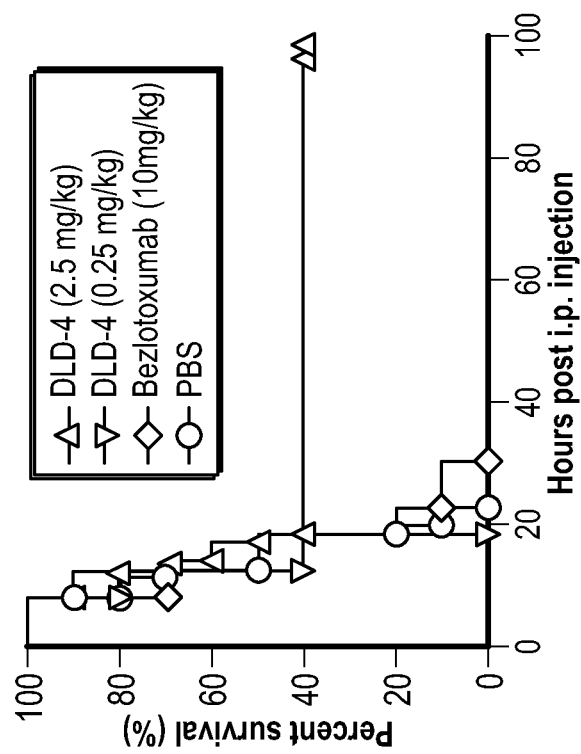
FIG. 9A shows mice that were i.p. injected with TcdB (1.5 µg/kg) alone (PBS, n=10), or together with DLD-4 (SEQ ID NO. 37) (0.25 or 2.5 mg/kg, n=10), or bezlotoxumab (10 mg/kg, n=10). Mouse survival rate was monitored, and data were analyzed by Kaplan-Meier survival analysis with Log rank test of significance. P=0.04 (DLD-4 (SEQ ID NO. 37) vs PBS).

Combining phage panning and functional screening, 12 DARPins that protected Vero cells against the TcdB-induced cytopathic effect at nanomolar concentrations were identified. A secondary functional screening of dimeric DARPins yielded 10 dimers with >100-fold improved toxin neutralization potency relative to the constituent monomers. FIG. 4 illustrates DARPin dimers exhibit superior toxin-neutralization potency relative to the constituent monomers. IMAC-purified DARPin dimers or monomers were added to Vero cells ($1.5 \times 10^3$ cells/well) together with TcdB toxin (5 µg/mL). Cell viability was quantified 72 hours later by CellTiterGlo assay and normalized to naïve Vero cells. Error bars represent the standard deviation of at least two independent experiments performed in duplicate. The best dimer DARPin, DLD-4 (SEQ ID NO. 37) (including U3 (SEQ ID NO. 13) and 1.4E (SEQ ID NO. 02), neutralized TcdB from VPI 10463 (ribotype 087) and M68 (ribotype 017) with $EC_{50}$ values of 4 and 16 pM respectively, representing a $\sim 330$-fold and $\sim 33$-fold higher potency than the FDA-approved bezlotoxumab in the same assay (FIG. 6). DLD-4 (SEQ ID NO. 37) effectively protected mice from a lethal i.p. TcdB toxin challenge (FIG. 9A). However, due to the surprisingly poor resistance of DLD-4 (SEQ ID NO. 37) against digestion by trypsin and chymotrypsin, no significant protection was observed in the mouse toxin cecum injection model (FIG. 9B). As such, the present disclosure envisions improving the protease stability of DLD-4 (SEQ ID NO. 37).

Functional Screening of TcdB-Neutralizing DARPins

Pooled DARPin variants from the 3rd round of phage panning were subcloned into the pET26b vector (between NdeI and HindIII) for high-level DARPin expression (FIG. 1A). 764 individual clones of *E. coli* BL21(DE3) cells transformed with the enriched library were picked and grown in eight 96-deep well plates (1 mL/well) at 37° C. for 8-10 h. Fifty µL of the overnight culture were transferred to fresh plates containing 1 mL/well LB and grown to mid-log phase ($OD_{600} \sim 0.6$) ($\sim 3$ hours) prior to the addition of isopropyl β-d-1-thiogalactopyranoside (IPTG). The culture was shaken at 400 rpm and at 37° C. for 4 hours and was harvested by centrifugation at 1700×g for 20 minutes. The cell pellets were resuspended in 100 µL of PBS (1.8 mM $KH_2PO_4$, 10 mM $Na_2HPO_4$, 137 mM NaCl, 2.7 mM KCl, pH 7.4) supplemented with lysozyme (200 µg/mL), incubated at 37° C. for 30 minutes, subjected to 3 cycles of freeze-thaw between 80° C. and 37° C., and centrifuged at 16,000×g for 10 minutes. The soluble fraction was transferred to fresh 96-well deep plates and incubated at 70° C. for 20 minutes and centrifuged again, yielding highly enriched DARPin in the supernatant. The supernatant was transferred to fresh plates and stored at −80° C. until use.

The semi-purified DARPin (0.1-10 µL lysate) was incubated with purified TcdB in growth medium (Dulbecco's Modified Eagle Medium (DMEM) supplemented with 10% fetal bovine serum (FBS), non-essential amino acids, penicillin (100 mg/mL) and 100 mM streptomycin) in 96-well plates for 2 hours at room temperature and then added to Vero cells seeded the night before in growth medium (final TcdB concentration 132 µg/mL). The concentration of TcdB was selected such that the viability of toxin-treated Vero cells was 10-20% that of naïve Vero cells after 6 hours of toxin contact time. Cell supernatants were replaced with fresh growth medium six hours later, and the cell viability was quantified 72 hours post toxin addition using CellTiter-Glo reagent (Promega) and normalized to Vero cells treated with the equivalent amount of lysate from untransformed BL21(DE3) cells in the absence of TcdB.

To create a dimeric DARPin library, monomeric DARPin variants identified from the functional library screening were PCR-amplified using Taq DNA polymerase (NEB) with two sets of primers. Set 1 used primers Ran2-D-F (SEQ ID NO. 44) and Linker-BSAi-D-R (SEQ ID NO. 47) (Table 1) to generate DARPins with a 3' linker sequence ((GGGGS)×3) (SEQ ID NO. 48), and Set 2 used primers Linker-BSAi-D-F (SEQ ID NO. 46) and Ran2-D-R (SEQ ID NO. 45) to generate DARPins with a 5' linker sequence. PCR products were digested with BsaI to generate sticky ends in the added linker region and ligated to form dimeric DARPins. This library was then inserted into the pET28a vector for expression in *E. coli*.

Table 1, shown below, illustrates primer sequences. Primers used to construct DARPin dimer library. Nucleotides binding to individual DARPins are indicated in lowercase. Primer Ran2-D-F (SEQ ID NO. 44) bound to the 5' end of each DARPin. Primer Ran2-D-R (SEQ ID NO. 45) binds to the 3' end of each DARPin. Primer Linker-BSAi-D-F (SEQ ID NO. 46) binds to the 5' end of each DARPin, adding a linker sequence and the BsaI restriction site to that end. Primer Linker-BSAi-D-R (SEQ ID NO. 47) binds to the 3' end of each DARPin, adding a linker sequence and the BsaI restriction site to that end. As such, primer Ran2-D-F (SEQ ID NO. 46) and a linker containing a Bsa I site were used to amplify a single DARPin, adding the linker and the BsaI site to the 3' end. Similarly, primer Ran2-D-R (SEQ ID NO. 45) and a linker containing a Bsa I site were used to amplify a single DARPin, adding the linker and the BsaI site to the 5' end.

TABLE 1

| Primer Name | Sequence |
| --- | --- |
| Ran2-D-F (SEQ ID NO. 44) | CAT GTG CAT T atctg ggatcc gacctgg |
| Ran2-D-R (SEQ ID NO. 45) | TAA CAG GCC GCA AGC TTT TAC GA |

TABLE 1-continued

| Primer Name | Sequence |
|---|---|
| Linker-BSAi-D-F (SEQ ID NO. 46) | ttagct ggtctc t ggagggagcggaggcggagggagcgctagc GAC CTG GGT AAG AAA CTG CTG |
| Linker-BSAi-D-R (SEQ ID NO. 47) | GAA ATC CTG CAA TCG AGC TCG gaattcggaggcggagggagcggaggc ggag t gagacc ttagct |

For the dimeric DARPin functional screen, the protocol was further simplified. 1504 individual clones of E. coli BL21(DE3) cells transformed with the dimeric DARPin library were picked and grown in 16 deep 96-well plates (1 mL/well) at 37° C. and 400 rpm in LB overnight. The next day, the cultures were harvested by centrifugation at 1700×g for 20 minutes. Each of the cell pellets was resuspended in 200 μL PBS supplemented with lysozyme (200 μg/mL) and incubated at 37° C. for 30 minutes. Next, the plates were subjected to 1 cycle of freeze-thaw between −80° C. and 37° C., and incubated at 70° C. for 20 minutes. The lysate was diluted in PBS and an equivalent of 0.2 μL of the undiluted lysate was added to Vero cells together with TcdB toxin (10 μg/mL) in a final volume of 100 μL. 72 hours later, the cell viability was quantified by CellTiterGlo assay and normalized to that of naïve Vero cells.

Protein Expression and Purification

E. coli BL21(DE3) cells transformed with DARPin expression plasmid (in pET26b) were cultured overnight at 37° C. in auto-induction media (6 g/L $Na_2HPO_4$, 3 g/L $KH_2PO_4$, 20 g/L tryptone, 5 g/L yeast extract, 5 g/L NaCl, 0.6% glycerol, 0.1% glucose, 0.08% lactose) supplemented with 50 μg/mL kanamycin. Cells were lysed by sonication. The lysate was clarified by centrifugation at 16,000×g for 10 minutes, and the soluble lysate was filtered through a 0.45 μm PES membrane and loaded onto a gravity Ni-NTA agarose column. The column was washed with PBS containing 15 mM imidazole and the bound proteins were eluted using PBS containing 150 mM imidazole. Protein purity was determined using SDS-PAGE.

DNA encoding bezlotoxumab VH and VL were synthesized and constructs encoded bezlotoxumab IgG1 light and heavy chains were transfected to CHO cells. The bezlotoxumab was purified from CHO supernatants using protein-A beads following a standard protocol.

In Vitro TcdB Neutralization Assay

Vero cells (1.5 or 2×103 cells/well) in growth medium were seeded in 96-well plates. The next day, serial dilutions of IMAC-purified DARPins were added to the appropriate wells followed by the addition of TcdB (final concentration 5 pg/mL or 2.5 pg/mL). The concentration of TcdB was selected such that the viability of the toxin-treated cells was 10-20% that of naïve Vero cells following 72 hours of toxin contact time. The plates were incubated at 37° C./5% CO2 for 72 hours. The cell viability was quantified using the CellTiter-Glo kit (Promega) following the manufacturer's instructions, or by quantifying the number of rounded cells. To quantify cell rounding, phase-contrast images were taken with an Olympus microscope. The numbers of normal and rounded cells in each image were determined by counting manually.

In Vivo TcdB Neutralization Activity of DARPins

Six to eight-week-old CD1 mice were purchased from Harlan Laboratories (MD, USA). All mice were housed in dedicated pathogen-free facilities in groups of 5 mice per cage under the same conditions. Food, water, bedding, and cages were autoclaved. All procedures involving mice were conducted under protocols approved by the Institutional Animal Care and Use Committees at the University of Maryland (IACUC #0517002). Mice judged to be in a moribund state were euthanized via carbon dioxide asphyxiation. DLD-4 (SEQ ID NO. 37) (2.5 mg/kg or 0.25 mg/kg), or bezlotoxumab (10 mg/kg) was mixed with TcdB (1.5 μg/kg) in PBS and incubated at room temperature for 1 h before being injected intraperitoneally (i.p.) into mice in the appropriate treatment groups. The control group was i.p. injected with TcdB alone in PBS. Mouse survival was monitored for 4 days until the termination of the experiments and data were analyzed by Kaplan-Meier survival analysis with Log rank test of significance. The cecum injection experiment was carried. Mice were anesthetized with intramuscular injection of a mixture of ketamin (100 mg/kg) and xylazine (10 mg/kg). The cecum, ileum and colon were exposed upon a midline laparotomy. IMAC-purified $TcdB_{VPI}$ (15 μg/mouse) or a mixture of $TcdB_{VPI}$ and DLD-4 (SEQ ID NO. 37) (5 mg/mouse) in PBS (100 μL) were injected directly into the cecum of mice via insulin syringes (29G) inserted into the ileocecal junction. The gut was returned to the abdomen after injection and the incision was closed with silk sutures. Mice were allowed to recover, and mouse survival were closely monitored for 72 hours.

Selection of Monomeric TcdB-Neutralizing DARPins

Figure 2A:
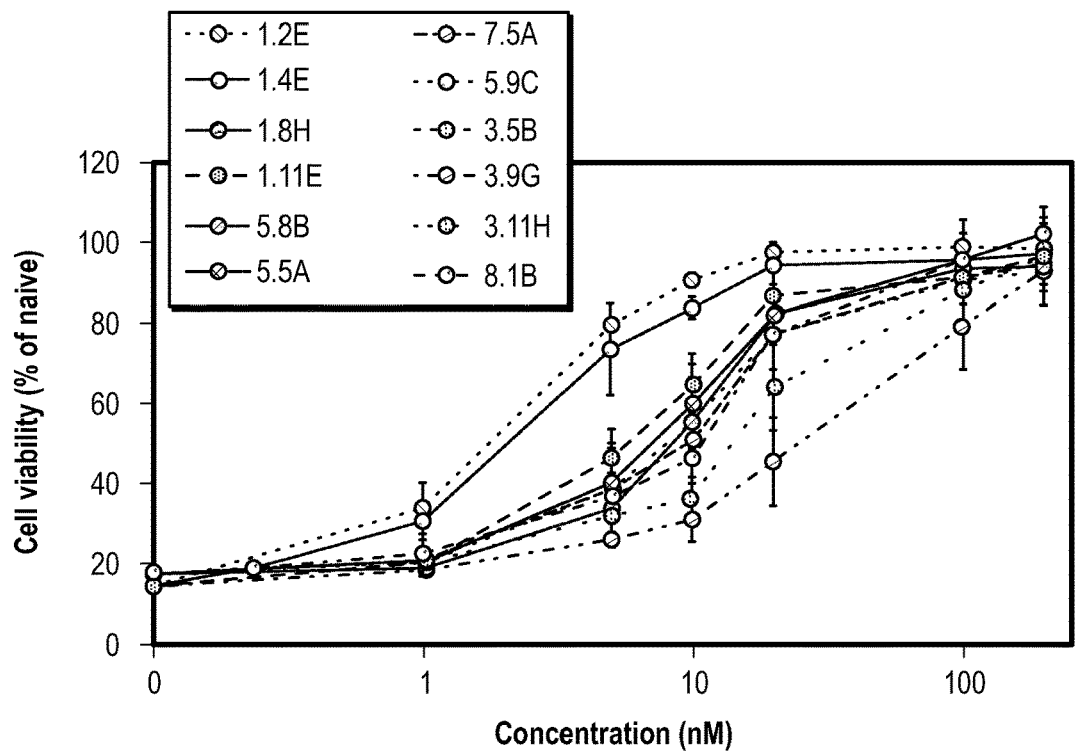
FIG. 2A, FIG. 2B, and FIG. 2C illustrate characterization of monomeric DARPins.
Figure 2B:
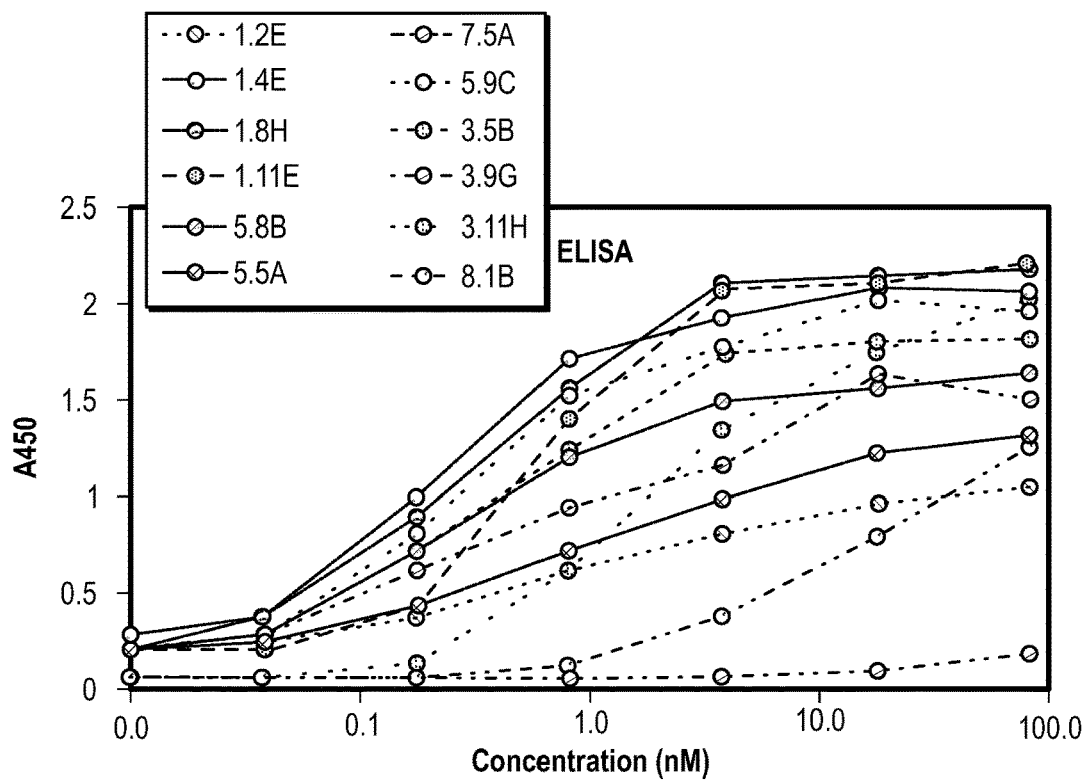
Figures 2C, 3A:
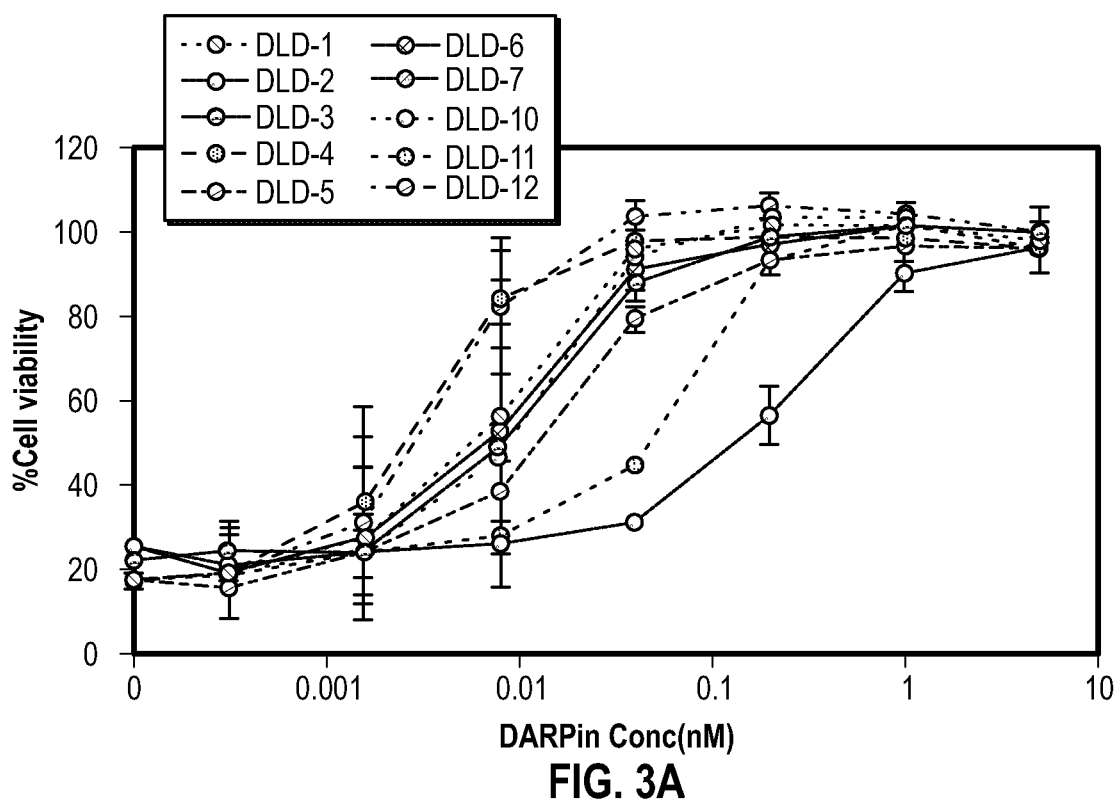
FIG. 3A, FIG. 3B, and FIG. 3C illustrate characterization of dimeric DARPins.

A library of approximately $2 \times 10^9$ DARPin variants was constructed via sequential PCR and ligation. Biotinylated TcdB (from C. difficile strain VPI10463) was used as the target protein to enrich DARPins that could bind the toxin via four rounds of phage panning. The enrich DARPin library pool from the 3rd round of phage panning were subcloned into the pET26b vector and transformed into E. coli BL21(DE3) cells for high-level DARPin expression and functional screening for those with toxin-neutralization ability. About 40% of the clones (299 clones) were able to rescue Vero cells viability from TcdB toxicity by >50%. The top 40 hits were sequenced and of which 12 were determined to be unique clones (FIG. 2, Table 2). FIG. 2A, FIG. 2B, and FIG. 2C illustrate characterization of monomeric DARPin. (A) Monomeric DARPins are able to protect Vero cells from TcdB-induced cytopathic effect at nanomolar concentrations. IMAC-purified DARPins were added to Vero cells ($2 \times 10^3$ cells/well) together with TcdB toxin (5 μg/mL). Cell viability was quantified 72 hours later by the CellTiterGlo assay and normalized to naïve Vero cells. Error bars represent the standard deviation of at least 2 independent experiments performed in duplicate. (B) Relative binding of DARPins to TcdB was determined using ELISA. Serially diluted DARPins were added to microtiter plates coated with 4 μg/mL of TcdB. Results are representative of 2 independent experiments. (C) DARPin monomer TcdB-neutralization potency. Data are the averages of at least 2 independent experiments. DARPin, designed ankyrin repeat protein; $EC_{50}$, half maximal effective concentration; ELISA, enzyme-linked immunosorbent assay; IMAC, Immobilized metal affinity chromatography; TcdB, C. difficile toxin B.

Most clones exhibited $EC_{50}$ values of ~10 nM, and the 2 best clones, 1.2E (SEQ ID NO. 01) and 1.4E (SEQ ID NO. 02), displayed $EC_{50}$ values of 2.4 nM and 3 nM, respectively. The relative affinity of each of the top 9 DARPins for TcdB was assessed by ELISA (FIG. 4B) and was found to not directly correlate with their in vitro neutralization potency. For example, although 1.2E (SEQ ID NO. 01) and 1.4E (SEQ ID NO. 02) neutralized TcdB with similar potency, 1.4E (SEQ ID NO. 02) appeared to be among the strongest toxin binders while 1.2E (SEQ ID NO. 01) was one of the weaker binders. The discrepancy between binding affinity and neutralization potency likely stems from the different epitopes engaged by the different DARPins. That is, a DARPin that weakly binds a region critical for toxin activity might exhibit a higher toxin-neutralization potency than another DARPin that binds strongly to a region of less importance.

Selection of Dimeric TcdB-Neutralizing DARPins

Figures 3B, 3C:
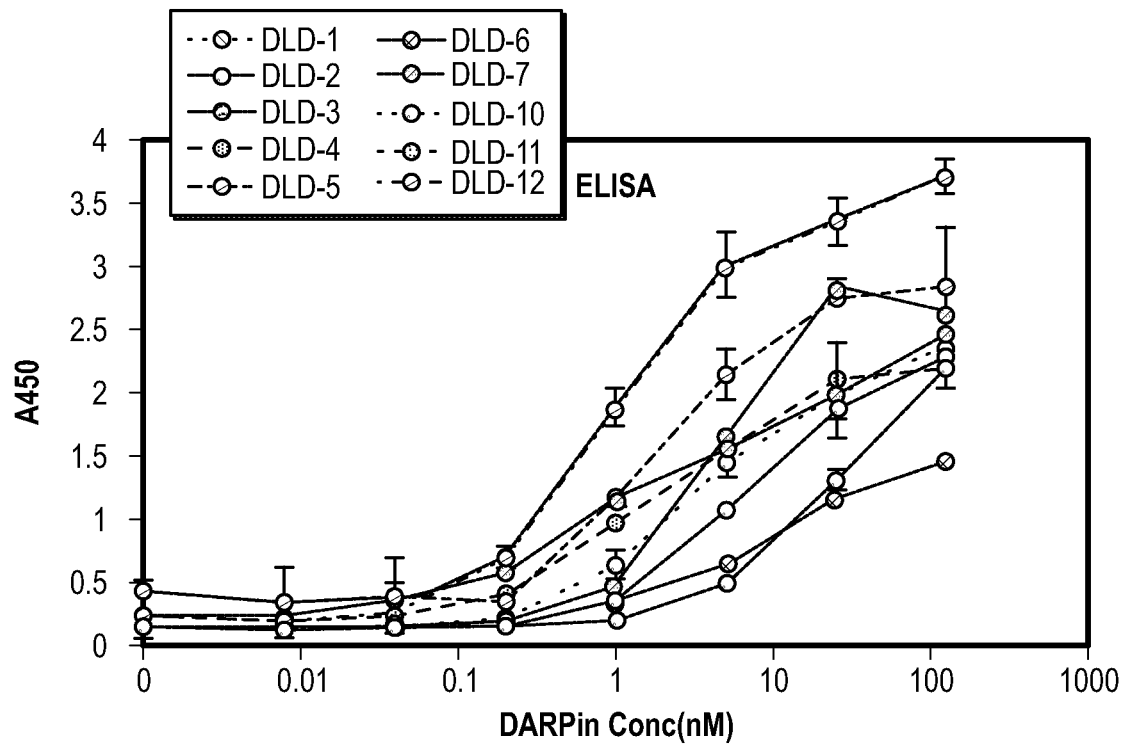
Figure 5:
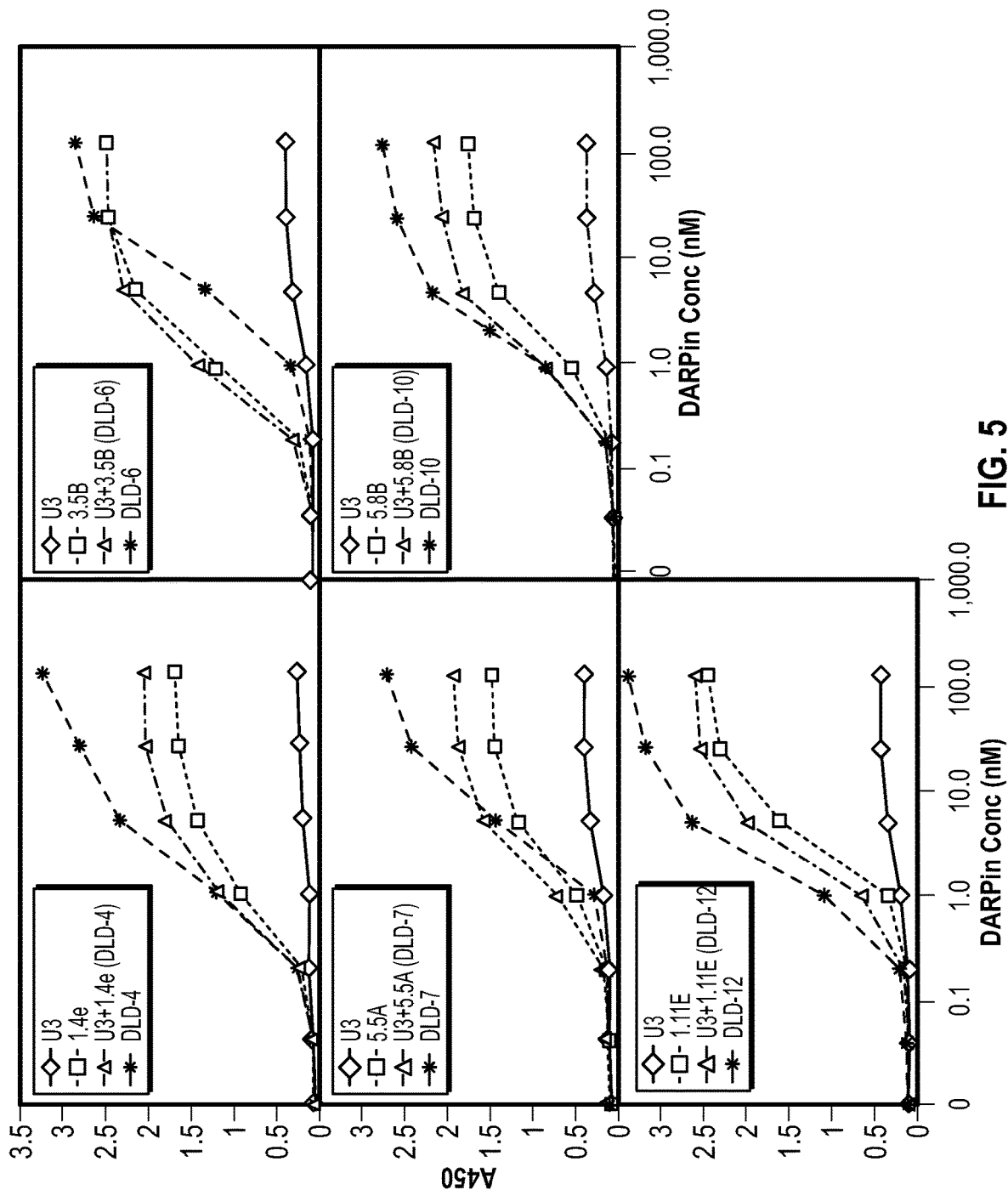
FIG. 5 illustrates DARPins dimers demonstrate avidity in TcdB binding. Binding of selected DARPin monomers, pooled monomers or dimers to TcdB was determined using ELISA. Combinations of serially diluted DARPins were added to microtiter plates coated with 4 µg/mL of TcdB. Results are representative of two independent experiments.

Fusion of multiple DARPins significantly enhances the target-binding affinity via avidity effects. It was hypothesized that fusion of two DARPins that bind non-overlapping epitopes on the toxin should yield enhanced binding affinity and thus a higher toxin-neutralization potency. A combinatorial library of DARPin dimers was created by joining individual monomeric DARPins (12 total) via a flexible linker (GGGGS×3) (SEQ ID NO. 48). A total of 1504 individual clones were screened using a Vero cell toxin challenge assay and 12 hits were identified. Of which, 10 were determined to be unique clones. The in vitro neutralization potencies of these 10 DARPins and their relative TcdB binding affinities are shown in FIG. 3. FIG. 3A, FIG. 3B, and FIG. 3C illustrate characterization of dimeric DARPins. FIG. 3A shows dimeric DARPins protect Vero cells from the TcdB-induced cytopathic effect at picomolar concentrations. IMAC-purified DARPin dimers were added to Vero cells ($1.5 \times 10^3$ cells/well) together with TcdB toxin (5 pg/mL). Cell viability was quantified 72 hours later by the CellTiterGlo assay and normalized to naïve Vero cells. Error bars represent the standard deviation of two independent experiments performed in duplicate. FIG. 3B shows relative binding of DARPins dimers to TcdB was determined using enzyme-linked immunosorbent assay (ELISA). Serially diluted DARPins were added to microtiter plates coated with 4 µg/mL of TcdB. Results are representative of two independent experiments and the error bars represent mean deviation from duplicate samples. FIG. 3C shows TcdB neutralization potency of DARPin dimers. Data are the averages of at least two independent experiments. The best DARPin dimer, DLD-4 (SEQ ID NO. 37), exhibited a toxin-neutralization $EC_{50}$ of 4±1 pM, which is ~600-fold lower than the best monomeric DARPin, 1.2E (SEQ ID NO. 01) ($EC_{50}$ 2.4*0.5 nM). As seen with the DARPin monomers, the relative TcdB binding affinities of the DARPin dimers were found to not directly correlate with their neutralization potency. Sequencing results also revealed that many of the dimers contained a new DARPin, U3 (SEQ ID NO. 13) or U5 (SEQ ID NO. 14), that was not present amongst the original 12 monomers (FIG. 3C, Table 2). U5 (SEQ ID NO. 14) is identical to U3 (SEQ ID NO. 13) except that it lacks the third randomized ankyrin repeat domain. U3 (SEQ ID NO. 13) alone exhibits weak, but detectable, toxin-neutralization activity ($EC_{50}$>25 nM, FIG. 4) in Vero cells and toxin-binding ability (FIG. 5). FIG. 5 illustrates DARPins dimers demonstrate avidity in TcdB binding. Binding of selected DARPin monomers, pooled monomers or dimers to TcdB was determined using ELISA. Combinations of serially diluted DARPins were added to microtiter plates coated with 4 µg/mL of TcdB. Results are representative of two independent experiments. U3 (SEQ ID NO. 13) and U5 (SEQ ID NO. 14) likely represent a minor constituent of the initial pool used to create the dimer DARPin library and their discovery is highly serendipitous because 1) they bind to a neutralizing epitope and 2) the U3/U5 (SEQ ID NO. 13)/(SEQ ID NO. 14) neutralization epitope is adjacent to the epitope targeted by the other DARPin hits such that the linker used is of sufficient length to accommodate simultaneous binding to both epitopes.

To understand the reason for the dramatic improvement in activity, the five dimer DARPins with the strongest toxin neutralization potency were further characterized. The in vitro TcdB-neutralization potency of the DARPin dimers were first compared with their constituent monomers (FIG. 4). All these DARPin dimers significantly out-performed their individual constituent monomers as well as the combination of both monomers, indicative of synergistic activity. The relative binding affinity of DARPin dimers and monomers were further compared using ELISA. As shown in FIG. 5, except for DLD-6 (SEQ ID NO. 39), all the dimeric DARPins yielded an increase in the ELISA signal relative to the constitute monomers. This observation is consistent with the binding of non-overlapping epitopes on the toxin by the monomeric DARPins via an avidity effect. An exception is DLD-6 (SEQ ID NO. 39), which appeared to bind the toxin more weakly than its constituent DARPin 3.5B (SEQ ID NO. 10) at concentrations <25 nM. This result is somewhat unexpected, considering that the toxin-neutralization potency of DLD-6 (SEQ ID NO. 39) is >100 fold higher than that of 3.5B (SEQ ID NO. 10) ($EC_{50}$: 12.5 pM for DLD-6 (SEQ ID NO. 39) vs. 13.3 nM for 3.5B (SEQ ID NO. 10)). A sandwich ELISA assay confirmed that DLD-6 (SEQ ID NO. 39) lacks the ability to crosslink two different TcdB molecules, which would have been responsible for the difference between neutralization potency and binding result. Without being bound by theory, it is posited that the most possible cause of this discrepancy is that TcdB protein may exhibit less flexibility when immobilized on an ELISA plate, thus hindering the simultaneous interaction with both U3 (SEQ ID NO. 13) and 3.5B (SEQ ID NO. 10).

Characterization of TcdB Neutralization Potency of DARPins

Protein engineering work was conducted using TcdB from the laboratory strain of *C. difficile* VPI10463 (ribotype 087). Since there is a significant amount of amino acid sequence heterogeneity between different strains of *C. difficile* there is a need to develop broadly neutralizing DARPins. As a first step to address this need, the activity of selected DARPin dimers (DLD-4 (SEQ ID NO. 37), DLD-7 (SEQ ID NO. 40), DLD-11 (SEQ ID NO. 42), DLD-12 (SEQ ID NO. 43)) against TcdB from three different strains of *C. difficile*: VPI10463, M68 (ribotype 012) and UK1 (ribotype 027) was evaluated. All DARPins were effective against toxins from VPI10463 and M68 (FIG. 6). FIG. 6A and FIG. 6B illustrate DARPin dimers offer superior protection to Vero cells against the toxicity of TcdB from *C. difficile* strains VPI 10463 (ribotype 087) and M68 (ribotype 017). FIG. 6A shows IMAC-purified DARPins were added to Vero cells ($1.5 \times 10^3$ cells/well) together with TcdB toxin (2.5 pg/mL). Cell viability was quantified 72 hours later by the CellTiterGlo assay and normalized to naïve Vero cells. Error bars represent the standard deviation of at least two independent experiments done in duplicate. Bezlotoxumab is the FDA-approved monoclonal antibody for treating recurrent *C. difficile* infection. a-GFP is a GFP-binding DARPin and was used here as a negative control. FIG. 6B shows DARPin dimer TcdB neutralization potency. Data are the averages of at least two independent experiments. The best DARPin, DLD-4 (SEQ ID NO. 37), was found to be ~330- and ~33-fold more efficacious than bezlotoxumab at inhibiting TcdB from VPI 10463 and M68, respectively, as quantified using the CellTiter-Glo assay (FIG. 6B). The $EC_{50}$s of DLD-4 (SEQ ID NO. 37) and bezlotoxumab were further measured using the conventional cell rounding assay, and were found to be similar to that determined using CTG assay (FIG. 7). FIG. 7A, FIG. 7B, and FIG. 7C illustrate DARPins dimers offer superior inhibition of TcdB from C. difficile strain VPI 10463 (ribotype 087). IMAC-purified DARPin dimer DLD-4 (SEQ ID NO. 37) or bezlotoxumab at were added to (1.5×103 cells/well) Vero cells (1.5×103 cells/well) together with TcdB (5 pg/mL). Cell viability was quantified 72 hours later using a cell rounding assay (FIG. 7A) or the CellTiterGlo assay (FIG. 7B) and normalized to naïve Vero cells. FIG. 7C shows TcdB neutralization potency. Error bars represent the standard deviation of duplicate wells. Data presented is representative of two independent experiments.

FIG. 8A and FIG. 8B illustrate in vivo studies. FIG. 8 (A and B) DARPins strongly exhibited the ability to neutralize (A) and bind (B) the different TcdB toxins. conc., concentration. (C) TcdB neutralization potency of different DARPins and bezlotoxumab. For neutralization assays, serially diluted immobilized-metal affinity chromatography (IMAC)-purified DARPins were mixed with the appropriate toxin and then added to Vero cells seeded the night before in 96-well plates. The cell viability was quantified by the CellTiterGlo assay 72 h later and normalized to naïve Vero cells. For ELISAs, the MaxiSorp plates were coated with the appropriate toxin followed by treatment with serially diluted DARPins. The amounts of plate-bound DARPins (containing Myc tags) were quantified using an anti-c-Myc antibody. Data in panel A represent averages of results from at least 2 independent experiments. Data presented in panel B are representative of results from two independent experiments performed in duplicate. FIG. 8A shows mice were i.p. injected with TcdB (1.5 µg/kg) alone (phosphate-buffered saline (PBS), n=10), or together with DLD-4 (SEQ ID NO. 37) (0.25 or 2.5 mg/kg, n=10), or bezlotoxumab (10 mg/kg, n=10). Mouse survival rate was monitored, and data were analyzed by Kaplan-Meier survival analysis with Log rank test of significance. P=0.04 (DLD-4 (SEQ ID NO. 37) vs PBS). FIG. 8B shows DLD-4 (SEQ ID NO. 37) (5 mg/mouse) was mixed with TcdB (15 µg/mouse) in 100 µL PBS and injected immediately into the cecum of mice (n=7). The control group received the same dose of TcdB alone (n=10). Mouse survival was monitored for 3 days and the data were analyzed by Kaplan-Meier survival analysis. P=0.349 (TcdB only vs. TcdB+DLD-4 (SEQ ID NO. 37)).

However, these DARPins showed negligible activity against TcdB from the UK1 strain, which belongs to the hypervirulent 027 ribotype. Bezlotoxumab also showed significantly weaker, albeit detectable, neutralization activity against this toxin ($EC_{50}>25$ nM). All the other DARPins were tested and it was found that five of them (i.e. 3.9G (SEQ 30 ID NO. 12), 1.2E (SEQ ID NO. 01), 8.1B (SEQ ID NO. 11), 1.8H (SEQ ID NO. 03) and 1.4E (SEQ ID NO. 02)) showed weak but detectable neutralization against $TcdB_{UK1}$.

The ability of the most potent anti-toxin DARPin, DLD-4 (SEQ ID NO. 37), to protect mice from systemic toxin challenge in vivo using two murine TcdB challenge models was further evaluated. In the first model, a lethal dose of TcdB (1.5 µg/kg) was mixed with DLD-4 (SEQ ID NO. 37) (0.25 or 2.5 mg/kg), bezlotoxumab (10 mg/kg) or PBS and then injected intraperitoneally (i.p.) into CD1 mice (5-10 mice/group). 40% of the mice survived after injection with the mixture containing the toxin mixed with 2.5 mg/kg DLD-4 (SEQ ID NO. 37) (p=0.04) (FIG. 9A). These results suggest that DLD-4 (SEQ ID NO. 37) possesses significant toxin-neutralization ability in vivo. Bezlotoxumab at 10 mg/kg dose did not show any protection against TcdB in this experiment nor in experiments where lower dosages of TcdB were used. This result is not particularly surprising considering that, in the phase III clinical trial, bezlotoxumab did not increase the initial clinical cure rate of CDI and was only approved by the FDA for reducing the recurrence of CDI, not as a treatment. The spore challenge model was not attempted because it was desired to de-couple in vivo anti-toxin activity from half-life and, unlike antibodies, unmodified DARPins suffer from a very short circulation half-life in vivo due to their small size.

The second model is the murine cecum injection model. A minor survival advantage (not statistically significant) was observed for mice receiving TcdB and DLD-4 (SEQ ID NO. 37) compared to TcdB alone (FIG. 9B). Further studies revealed that the less-than-expected in vivo efficacy of DLD-4 (SEQ ID NO. 37) in this cecum injection model was most likely due to its poor protease stability. Specifically, DARPin DLD-4 (SEQ ID NO. 37) is sensitive to digestion by trypsin and chymotrypsin, the most abundant protease in the gastrointestinal tract.

Dimeric DARPins with Enhanced Potency Against $TcdB_{VPI}$ and $TcdB_{M68}$

Figure 10A:
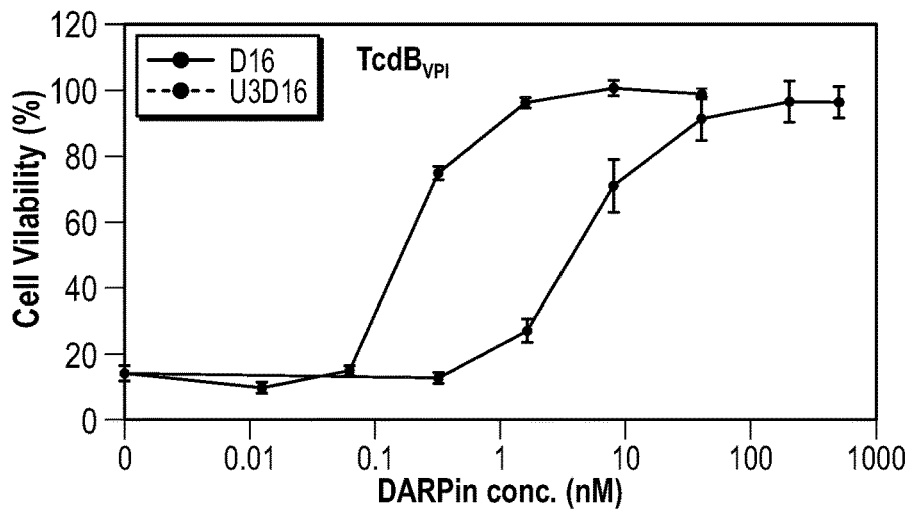
FIG. 10A and FIG. 10B show DARPin dimer U3D16 (SEQ ID NO. 49) displaying enhanced neutralization ability against TcdB$_{VPI}$ (FIG. 10A) and TcdB$_{M68}$ (FIG. 10B).
Figure 10B:
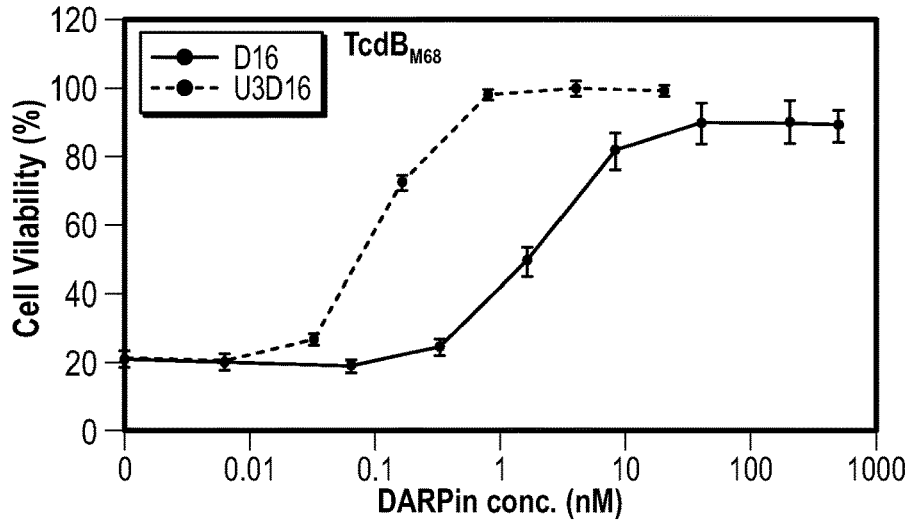
Figure 10C:
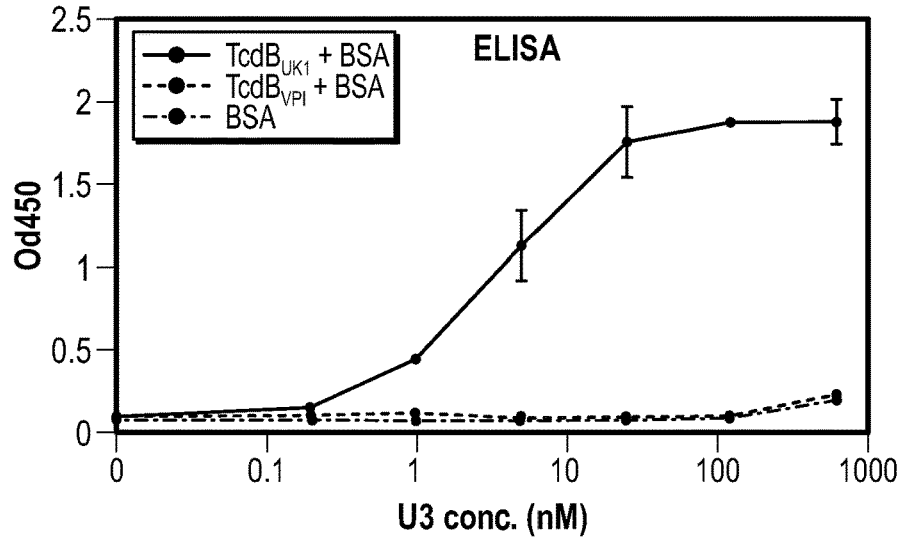
FIG. 10C shows that U3 (SEQ ID NO. 13) lacks the ability to bind to TcdB$_{UK1}$ as determined by ELISA.

Fusion of multiple binders to non-overlapping epitopes has been reported to significantly enhance the overall target-binding affinity via the avidity effect. DARPin U3 (SEQ ID NO. 13) which interferes with the interaction between TcdB and its receptor FZD1/2/7 was identified. Dimer DARPin—DLD-4 (SEQ ID NO. 37)—containing U3 (SEQ ID NO. 13) and 1.4E (SEQ ID NO. 02) joined by a 3×GGGGS (SEQ ID NO. 48) linker exhibited >100-fold higher neutralization potency against $TcdB_{VPI}$ than either constituent monomer. Since both D16 (SEQ ID NO. 23) and 1.4E (SEQ ID NO. 02) interfere TcdB-CSPG4 interaction, it was reasoned that a dimeric DARPin having U3 (SEQ ID NO. 13) and D16 (SEQ ID NO. 23) joined by the same linker should exhibit stronger toxin-neutralization potency than D16 (SEQ ID NO. 23) alone. Indeed, the dimeric DARPin U3D16 (SEQ ID NO. 49) showed 10-20-fold higher activity toward $TcdB_{VPI}$ and $TcdB_{M68}$ than D16 (SEQ ID NO. 21) alone (FIG. 10A and FIG. 10B). In addition, subsequent ELISA studies confirmed that U3 (SEQ ID NO. 13) lacks the ability to bind $TcdB_{UK1}$ (FIG. 10C). FIG. 10A and FIG. 10B show DARPin dimer U3D16 (SEQ ID NO. 49) showed enhanced neutralization ability against $TcdB_{VPI}$ (FIG. 10A) and $TcdB_{M68}$ (FIG. 10B). The error bars represent mean deviation from 2 independent experiments. The data is representative of two independent experiments performed in duplicate. FIG. 10C shows U3 (SEQ ID NO. 13) lacks the ability to bind to $TcdB_{UK1}$ as determined by ELISA. The ELISA plates were coated with $TcdB_{UK1}$ or $TcdB_{VPI}$ and blocked with bovine serum albumin (BSA). The data is representative of two independent experiments performed in duplicate.

DARPin Interactions

Figure 11A:
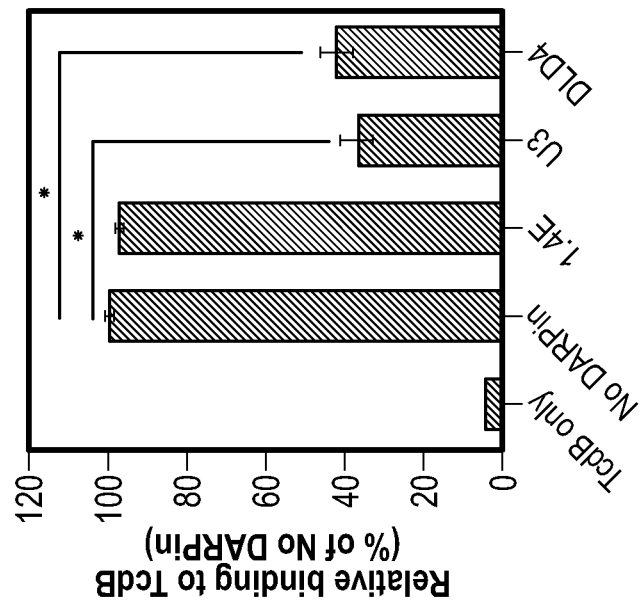
FIG. 11A and FIG. 11B illustrate that DARPin DLD-4 (SEQ ID NO. 37) blocks the interaction between TcdB and its cellular receptors.
Figure 11B:
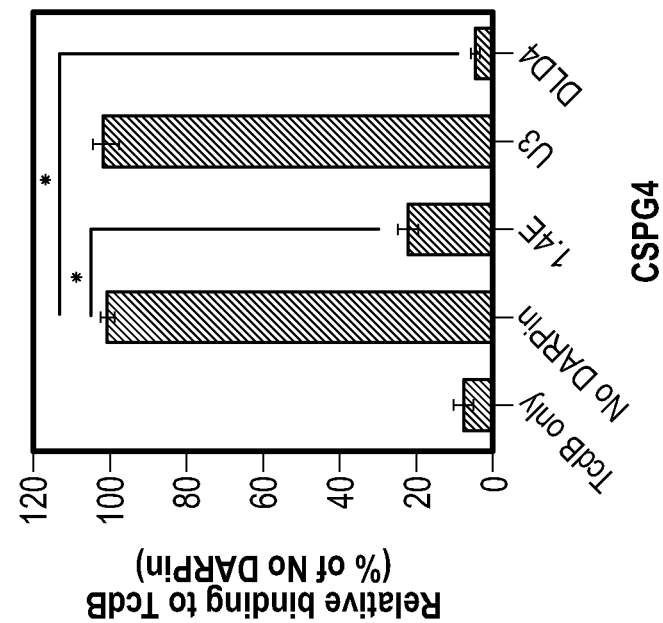

DARPin DLD-4 (SEQ ID NO. 37) blocks the interaction between TcdB and its cellular receptors (FIG. 11). ELISA plates were coated with $TcdB_{VPI}$ followed by treatment with the 1 nM of the extracellular domains of Chondroitin Sulfate Proteoglycan 4 (CSPG4) (FIG. 10A), or Frizzled Class Receptor 2 (FZD2) (FIG. 11B) alone or in mixture with 250 nM of the indicated DARPins. The amount of TcdB-bound CSPG4 and FZD2 was detected using the respective antibodies. Data was normalized to each receptor binding to TcdB in the absence of DARPins (No DARPin). Both 1.4E (SEQ ID NO. 02) and DLD-4 (SEQ ID NO. 37) blocked the interaction between CSPG4 and TcdB, while U3 (SEQ ID NO. 13) had no significant effect on the TcdB-CSPG4 interaction. Similarly, U3 (SEQ ID NO. 13) and DLD-4 (SEQ ID NO. 37) significantly blocked the interaction between FZD2 and TcdB, but not 1.4E (SEQ ID NO. 02).

FIG. 11A and FIG. 11B illustrate DARPin DLD-4 (SEQ ID NO. 37) blocks the interaction between TcdB and its cellular receptors. ELISA plates were coated with TcdB$_{VPI}$ followed by treatment with the 1 nM of the extracellular domains of Chondroitin Sulfate Proteoglycan 4 (CSPG4) (FIG. 11A), or Frizzled Class Receptor 2 (FZD2) (FIG. 11B) alone or in mixture with 250 nM of the indicated DARPins. The amount of TcdB-bound CSPG4 and FZD2 was detected using the respective antibodies. Data was normalized to each receptor binding to TcdB in the absence of DARPins (No DARPin). Both 1.4E (SEQ ID NO. 02) and DLD-4 (SEQ ID NO. 37) blocked the interaction between CSPG4 and TcdB, while U3 (SEQ ID NO. 13) had no significant effect on the TcdB-CSPG4 interaction. Similarly, U3 (SEQ ID NO. 13) and DLD-4 (SEQ ID NO. 37) significantly blocked the interaction between FZD2 and TcdB, but not 1.4E (SEQ ID NO. 02). Error bars represent the standard deviation of three independent experiments done in duplicate. *: $p<0.005$, t-test.

Figure 12A:
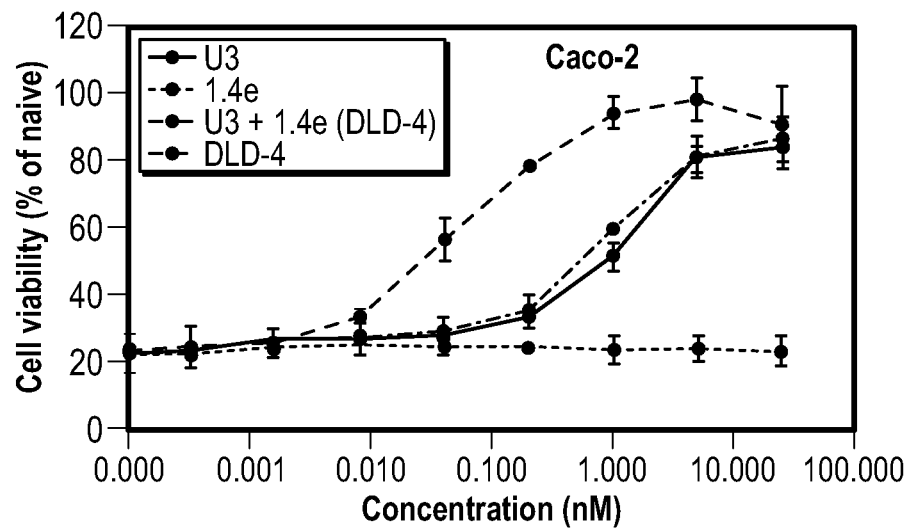
FIG. 12A and FIG. 12B show DARPin DLD-4 (SEQ ID NO. 37) inhibits TcdB from *C. difficile* strains VPI 10463 (ribotype 087) in Caco-2 and TZM cells.
Figure 12B:
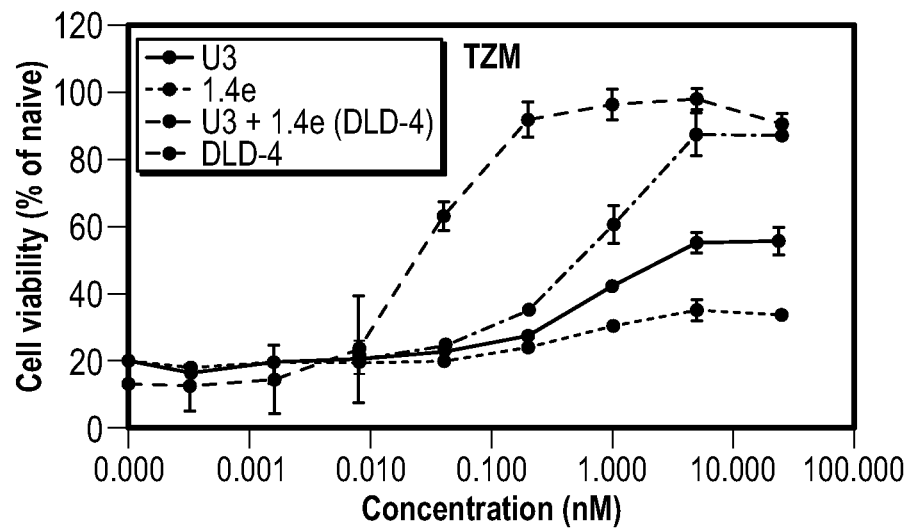

DARPin DLD-4 (SEQ ID NO. 37) inhibits TcdB from *C. difficile* strains VPI 10463 (ribotype 087) in Caco-2 and TZM cells (FIG. 12). IMAC-purified DARPins were added to Caco-2 cells (1.5×103 cells/well) together with 10 μg/mL TcdB. Cell viability was quantified 72 hours later by the CellTiterGlo assay and normalized to naïve Caco-2 cells. Only U3 (SEQ ID NO. 13) and DLD-4 (SEQ ID NO. 37) inhibited TcdB cytotoxicity in these cells (FIG. 14A). IMAC-purified DARPins were added to TZM cells (1.5×103 cells/well) together with 5 pg/mL TcdB. Cell viability was quantified 72 hours later by the CellTiterGlo assay and normalized to naïve TZM cells. U3 (SEQ ID NO. 13) and 1.4E (SEQ ID NO. 02) showed partial inhibition of TcdB in TZM cells (FIG. 12B). FIG. 12A and FIG. 12B show DARPin DLD-4 (SEQ ID NO. 37) inhibits TcdB from *C. difficile* strains VPI 10463 (ribotype 087) in Caco-2 and TZM cells. FIG. 12A shows IMAC-purified DARPins were added to Caco-2 cells (1.5×103 cells/well) together with 10 pg/mL TcdB. Cell viability was quantified 72 hours later by the CellTiterGlo assay and normalized to naïve Caco-2 cells. Only U3 (SEQ ID NO. 13) and DLD-4 (SEQ ID NO. 37) inhibited TcdB cytotoxicity in these cells. Error bars represent the standard deviation of two independent experiments done in duplicate. FIG. 12B shows IMAC-purified DARPins were added to TZM cells (1.5×10, cells/well) together with 5 pg/mL TcdB. Cell viability was quantified 72 hours later by the CellTiterGlo assay and normalized to naïve TZM cells. U3 (SEQ ID NO. 13) and 1.4E (SEQ ID NO. 02) showed partial inhibition of TcdB in TZM cells. Error bars represent the standard deviation of two independent experiments done in duplicate.

Enhanced Stability Against Proteases

Figure 13A:
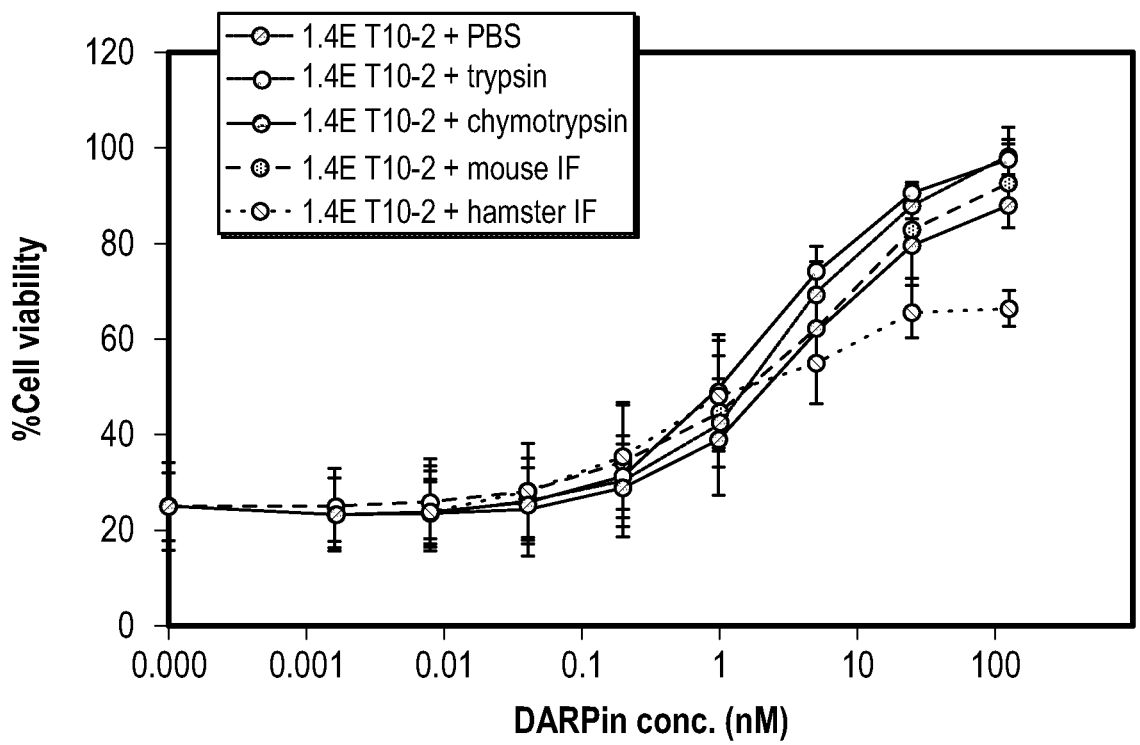
FIG. 13A and FIG. 13B show that DARPin 1.4E T10-2 (SEQ ID NO. 32) and 1.4E C3 (SEQ ID NO. 33) exhibit enhanced stability against proteases.
Figure 13B:
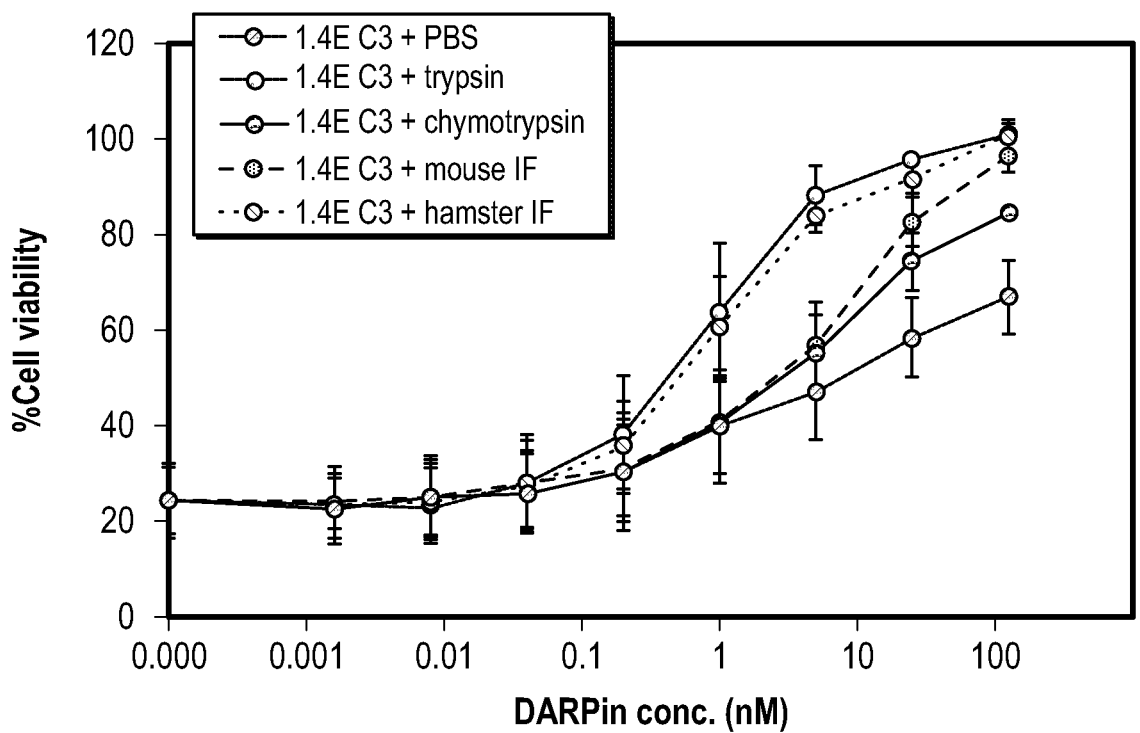

FIG. 13A and FIG. 13B show that DARPin 1.4E T10-2 (SEQ ID NO. 32) and 1.4E C3 (SEQ ID NO. 33) exhibit enhanced stability against proteases. Purified 1.4E T10-2 (SEQ ID NO. 32) (FIG. 13A) and 1.4E C3 (SEQ ID NO. 33) (FIG. 13B) were incubated with 1 mg/ml trypsin, 0.5 mg/ml chymotrypsin, an equal volume of intestinal fluid (IF) from mouse or hamster, or PBS at 37 C for one hour before being serially diluted and added to Vero cells together with TcdB (5 pg/mL). Cell viability was quantified 72 hours later and normalized to naïve Vero cells. DARPin 1.4E T10-2 (SEQ ID NO. 32) and 1.4E C3 (SEQ ID NO. 33) exhibit enhanced stability against proteases (FIG. 13). Purified 1.4E T10-2 (SEQ ID NO. 32) (FIG. 13A) and 1.4E C3 (SEQ ID NO. 33) (FIG. 13B) were incubated with 1 mg/ml trypsin, 0.5 mg/nil chymotrypsin, an equal volume of intestinal fluid (IF) from mouse or hamster, or PBS at 37 C for one hour before being serially diluted and added to Vero cells together with TcdB (5 pg/mL). Cell viability was quantified 72 hours later and normalized to naïve Vero cells.

Table 2, shown below, illustrates the monomer, dimer, primer, and linker sequence listings of the present disclosure.

TABLE 2

Monomer Sequences 1.2E
(SEQ ID NO. 01)
GSDLGKKLLEAARAGQDDEVRILMANGADVNAYDARGVTPLHLAAFSGHL
EIVEVLLKNGADVNAIDVIGMTPLHLAAWIGHLEIVEVLLKHGADVNAVD
RSGNTPLHLAAWLGHLEIVEVLLKYGADVNAQDKFGKTAFDISIDNGNED
LAEILQSSS 1.4E
(SEQ ID NO. 02)
GSDLGKKLLEAARAGQDDEVRILMANGADVNATDHLGVTPLHLAAVLGHL
EIVEVLLKHGADVNAYDILGRTPLHLAAWRGHLEIVEVLLKYGADVNADD
TSGTTPLHLAAGEGHLEIVEVLLKYGADVNAQDKFGKTAFDISIDNGNED
LAEILQSSS 1.8H
(SEQ ID NO. 03)
GSDLGKKLLEAARAGQDDEVRILMANGADVNAIDALGVTPLHLAAWVGHL
EIVEVLLKNGADVNAVDVLGWTPLHLAAWKGHLEIVEVLLKHGADVNAMD
NRGPTPLHLAAVDGHLEIVEVLLKNGADVNAQDKFGKTAFDISIDNGNED
LAEILQSSS 1.11E
(SEQ ID NO. 04)
GSDLGKKLLEAARAGQDDEVRILMANGADVNATDHLGVTPLHLAAVLGHL
EIVEVLLKHGADVNAYDILGRTPLHLAAWRGHLEIVEVLLKYGADVNAVD
TMGETPLHLAAGMGHLEIVEVLLKHGADVNAQDKFGKTAFDISIDNGNED
LAEILQSSS 5.8B
(SEQ ID NO. 05)
GSDLGKKLLEAARAGQDDEVRILMANGADVNALDTHGVTPLHLAAWRGHL
EIVEVLLKNGADVNAGDVLGRTPLHLAATFGHLEIVEVLLKHGADINAVD
TVGVTPLHLAAGQGHLEIVEVLLKYGADVNAQDKFGKTAFDISIDNGNED
LAEILQSSS 5.5A
(SEQ ID NO. 06)
GSDLGKKLLEAARAGQDDEVRILMANGADVNAVDRAGTTPLHLAAHGGHL
EIVEVLLKYGADVNARDLLGRTPLHLAAWRGHLEIVEVLLKHGADVNASD
PLGITPLHLAAATGHLEIVEVLLKNGADVNAQDKFGKTAFDISIDNGNED
LAEILQSSS 7.5A
(SEQ ID NO. 07)
GSDLGKKLLEAARAGQDDEVRILMANGADVNALDTHGVTPLHLAAWRGHL
EIVEVLLKNGADVNAGDVLGRTPLHLAATFGHLEIVEVLLKHGADVNAVD
TVGVTPLHLAAGQGHLEIVEVLLKYGADVNAQDKFGKTAFDISIDNGNED
LAEILQSSS 5.9C
(SEQ ID NO. 08)
GSDLGKKLLEAARAGQDDEVRILMANGADVNAQDYYGSTPLHLAAWLGHL
EIVEVLLKNGADVNAGDLLGRTPLHLAAWFGHLEIVEVLLKHGADVNAVD
TMGETPLHLAAGMGHLEIVEVLLKHGADVNAQDKFGKTAFDISIDNGNED
LAEILQSSS 3.11H
(SEQ ID NO. 09)
GSDLGKKLLEAARTGQDDEVRILMANGADVNAKDEGGPTPLHLAAVGGHL
EIVEVLLKHGADVNAVDALGRTPLHLAAWQGHLEIVEVLLKHGADVNARD
KNGYTPLHLAAGMGHLEIVEVLLKYGADVNAQDKFGKTAFDISIDNGNED
LAEILQSSS 3.5B
(SEQ ID NO. 10)
GSDLGKKLLEAARAGQDDEVRILMANGADVNAKDTFGETPLHLAAWKGHL
EIVEVLLKYGADVNASDLLGRTPLHLAAWRGHLEIVEVLLKNGADVNASD
TGGYTPLHLAAALGHLEIVEVLLKHGADVNAQDKFGKTAFDISIDNGNED
LAEILQSSS TABLE 2-continued 8.1B
(SEQ ID NO. 11)
GSDLGKKLLEAARAGQDDEVRILMANGADVNAKDGSGVTPLHLAAVAGHL
EIVEVLLKNGADVNARDRLGRTPLHLAAWRGHLEIVEVLLKNGADVNAKD
LGGDTPLHLAAALGHLEIVEVLLKNGADVNAQDKFGKTAFDISIDNGNED
LAEILQSSS 3.9G
(SEQ ID NO. 12)
GSDLGKLLEAARAGQDDEVRILMANGADVNANDRRGITPLHLAAINGHLE
IVEVLLKNGADVNAVDVLGFTPLHLAAWRGHLEIVEVLLKNGADVNAFDK
SGSTPLHLAAHFGHLEIVEVLLKYGADVNAQDKFGKTAFDISIDNGNEDL
AEILQSSS U3
(SEQ ID NO. 13)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDSGNEDLA
EILQSSS U5
(SEQ ID NO. 14)
GSDLGKKLLEAARAGQDDEVRILMANGADVNADDRIGMTPLHLAAIGGHL
EIVEVLLKNGADVNADDVHGRTPLHLAAGRGHLEIVEVLLKNGADVNAQD
KFGKTAFDISIDNGNEDLAEILQSSS TEMP
(SEQ ID NO. 15)
GSDLGKKLLEAARAGQDDEVRILMANGADVNANDRRGITPLHLAAINGHL
EIVEVLLKNGADVNAVDVLGFTPLHLAAWRGHLEIVEVLLKNGADVNAFD
KSGSTPLHLAAHFGHLEIVEVLLKYGADVNAQDKFGKTAFDISIDNGNED
LAEILQSSS D3
(SEQ ID NO. 16)
GSDLGKKLLEAARAGQDDEVRILMANGADVNAADRYGPTPLHLAAYRGHL
EIVEVLLKHGADVNAKDVLGWTPLHLAAWIGHLEIVEVLLKNGADVNAVD
VTGETPLHLAAVMGHLEIVEVLLKHGADVNAQDKFGKTAFDISIDNGNED
LAEILQSSS D10
(SEQ ID NO. 17)
GSDLGKKLLEAARAGQDDEVRILMANGADVNAADRYGPTPLHLAAYRGHL
EIVEVLLKHGADVNAKDVLGWTPLHLAAWIGHLEIVEVLLKNGADVNAVD
VTGETPLHLAAVMGHLEIAEVLLKHGADVNAQDKFGKTAFDISIDNGNED
LAEILQSSS D13
(SEQ ID NO. 18)
GSDLGKKLLEAARAGQDDEVRILVANGADVNAADRYGPTPLHLAAYRGHL
EIVEVLLKHGADVNAKDVLGWTPLHLAAWIGHLEIVEVLLKNGADVNAVD
VTGETPLHLAAVMGHLEIVEVLLKHGADVNAQDKFGKTAFDISIDNGNED
LAEILQSSS D7
(SEQ ID NO. 19)
GSDLGKKLLEAARAGQDDEVRILMANGADVNAADRYGPTPLHLAAYRGHL
EIVEVLLKHGADVNAKDVLGWTPLHLAAWIGHPEIVEVLLKNGADVNAVD
VTGETPLHLAAVMGHLEIVEVLLKHGADVNAQDKFGKTAFDISIDNGNED
LAEILQSSS D9
(SEQ ID NO. 20)
GSDLGKKLLEAARAGQDDEVRILMANGADVNAADRYGPTPLHLAAYRGHL
EIAEVLLKHGADVNAKDVLGWTPLHLAAWIGHLEIVEVLLKNGADVNAVD
VTGETPLHLAAVMGHLEIVEVLLKHGADVNAQDKFGKTAFDISIDNGNED
LAEILQSSS D6
(SEQ ID NO. 21)
GSDLGKKLLEAARAGQDDEVRILMANGADVNAADRYGPTPLHLAAYRGHL
EIVEVLLKHGADVNAKDVLGWTPLHLAAWIGHLEIVEVLPKNGADVNAVD
VTGETPLHLAAVMGHLEIVEVLLKHGADVNAQDKFGKTAFDISIDNGNED
LAEILQSSS D15
(SEQ ID NO. 22)
GSDLGKKLLEAARAGQDDEVRILMANGADVNAADRYGPTPLHLAAYRGHL
EIVEVLLKHGADVNAKDVLGWTPLHLAAWIGHLEIVEVLLKNGADVNAVD
VTGETPLHLAAVMGHLEIVEVLLKNGADVNAQDKFGKTAFDISIDNGNED
LAEILQSSS D16
(SEQ ID NO. 23)
GSDLGKKLLEAARAGQDDEVRILMANGADVNAADRYGPTPLHLAAYRGHL
EIVEVLLKHGADVNAKDVLGWTPLHLAAWIGHLEIVEVLLKNGADVNARD
RTGETPLHLAAAIGHLEIVEVLLKNGADVNAQDKFGKTAFDISIDNGNED
LAEILQSSS D8
(SEQ ID NO. 24)
GSDLGKKLLEAARAGQDDEVRILMANGADVNAADRYGPTPLHLAAYRGHL
EIVEVLLKHGADVNAKDLLGFTPVHLAAWLGHLEIVEVLLKNGADVNARD
RTGETPLHLAAAIGHLEIVEVLLKNGADVNAQDKFGKTAFDISIDNGNED
LAEILQSSS D14
(SEQ ID NO. 25)
GSDLGKKLLEAARAGQDDEVRILMANGADVNALDVRGSTPLHLAAYRGHL
EIVEVLLKNGADVNAKDLLGFTPVHLAAWLGHLEIVEVLLKNGADVNAGD
RTGETPLHLAAAIGHLEIVEVLLKNGADVNAQDKFGKTAFDISIDNGNED
LAEILQSSS D1
(SEQ ID NO. 26)
GSDLGKKLLEAARAGQDDEVRILMANGADVNALDVRGSTPLHLAAFKGHL
EIVEVLLKNGADVNAKDLLGFTPVHLAAWLGHLEIVEVLPKNGADVNARD
RTGETPLHLAAAIGHLEIVEILLKYGADVNAQDKFGKTAFDISIDNGNED
LAEILQSSS D2
(SEQ ID NO. 27)
GSDLGKKLLEAARAGQDDEVRILMANGADVNALDVRGSTPLHLAAFKGHL
EIVEVLLKNGADVNAKDLLGFTPVHLAAWLGHLEIVEVLLKNGADVNARD
RTGETPLHLAAAIGHLEIVEVLLKNGADVNAQDKFGKTAFDISIDNGNED
LAEILQSSS D4
(SEQ ID NO. 28)
GSDLGKKLLEAARAGQDGEVRILMANGADVNALDVRGSTPLHLAAFKGHL
EIVEVLLKNGADVNAKDLLGFTPVHLAAWLGHLEIVEVLLKNGADVNARD
RTGETPLHLAAAIGHLEIVEVLLKNGADVNAQDKFGKTAFDISIDNGNED
LAEILQSSS D12
(SEQ ID NO. 29)
GSDLGKKLLEAARAGQDDEVHILMANGADVNALDVRGSTPLHLAAFKGHL
EIVEVLLKNGADVNAKDLLGFTPVHLAAWLGHLEIVEVLLKNGADVNARD
RTGETPLHLAAAIGHLEIVEVLLKNGADVNAQDKFGKTAFDISIDNGNED
LAEILQSSS D5
(SEQ ID NO. 30)
GSDLGKKLLEAARAGQDDEVRILMANGADVNALDVRGSTPLHLAAFKGHL
EIVEVLLKNGADVDAKDLLGFTPVHLAAWLGHLEIVEVLLKNGADVNARD
RTGETPLHLAAAIGHLEIVEVLLKNGADVNAQDKFGKTASDISIDNGNED
LAEILQSSS D11
(SEQ ID NO. 31)
GSDLGKLLEAGRAGQDDEVRILMANGADVNALDVRGSTPLHLAAFKGHL
EIVEVLLKNGADVNAKDLLGFTPVHLAAWLGHLEIVEVLLRNGADVNARD
RTGETPLHLAAAIGHLEIVEVLLKNGADVNAQDKFGKTAFDISIDNGNED
LAEILQSSS 1.4E T10-2
(SEQ ID NO. 32)
GSDLGGLLLEAAQAGQDDEVHILMANGADVNTTDHLGVTPLHLAAVLGHL
EIVEVLLQHGADVNAYDILGRTPLHLAAWKGHLEIVEVLLQYGADVNADD
TSGTTPLHLAAAEGHLEIVEVLLQYGADVNAQDIFGTTASDISIDNGNED
LAEILQSSS

TABLE 2-continued 1.4E C3

(SEQ ID NO. 33)
GSDLGELLLEAAQAGQDDEVHILMANGADVNATNHLGVTPLHLAAVLGHL
EIVEVLLQHGADVNAIDILGRTPLHLAAWKGHLEIVEVLLQHGADVNADD
TSGTTPLHLAAGEGHLEIVEVLLQHGADVNAQDINGTTASDISIDNGNED
LAEILQSSS

Dimer Sequences

DLD-1

(SEQ ID NO. 34)
GSDLGKKLLEAARAGQDDEVRILMANGADVNAVDRAGTTPLHLAAHGGHL
EIVEVLLKYGADVNARDLLGRTPLHLAAWRGHLEIVEVLLKHGADVNASD
PLGITPLHLAAATGHLEIVEVLLKNGADVNAQDKFGKTAFDISIDNGNED
LAEILQSSSEFGGGGSGGGGSGGGGSASDLGKKLLEAARAGQDDGVRILM
ANGADVNALDTHGVTPLHLAAWRGHLEIVEVLLKNGADVNAGDVLGRTPL
HLAATFGHLEIVEVLLKHGADVNAVDTVGVTPLHLAAGQGHLEIVEVLLK
YGADVNAQDKFGKTAFDISIDNGNEDLAEILQSSS

DLD-2

(SEQ ID NO. 35)
GSDLGKKLLEAARAGQDDEVRILMANGADVNAIDALGVTPLHLAAWVGHL
EIVEVLLKNGADVNAVDVLGWTPLHLAAWKGHLEIVEVLLKHGADVNAMD
NRGPTPLHLAAVDGHLEIVEVLLKNGADVNAQDKFGKTAFDISIDNGNED
LAEILQSSSEFGGGGSGGGGSGGGGSASDLGKKLLEAARAGQDDEVRILM
ANGADVNAYDARGVTPLHLAAFSGHLEIVEVLLKNGADVNAIDVIGMTPL
HLAAWIGHLEIVEVLLKHGADVNAVDRSGNTPLHLAAWLGHLEIVEVLLK
YGADVNAQDKFGKTAFDISIDNGNEDLAEILQSSS

DLD-3

(SEQ ID NO. 36)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDSGNEDLA
EILQSSSEFGGGGSGGGGSGGGGSASDLGKKLLEAARAGQDDEVRILMAN
GADVNAQDYYGSTPLHLAAWLGHLEIVEVLLKNGADVNAGDLLGRTPLHL
AAWFGHLEIVEVLLKHGADVNAVDTMGETPLHLAAGMGHLEIVEVLLKHG
ADVNAQDKFGKTAFDISIDNGNEDLAEILQSSS

DLD-4

(SEQ ID NO. 37)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSASDLGKKLLEAARAGQDDEVRILMAN
GADVNATDHLGVTPLHLAAVLGHLEIVEVLLKHGADVNAYDILGRTPLHL
AAWRGHLEIVEVLLKYGADVNADDTSGTTPLHLAAGEGHLEIVEVLLKYG
ADVNAQDKFGKTAFDISIDNGNEDLAEILQSSS

DLD-5

(SEQ ID NO. 38)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAQD
KFGKTAFDISIDNGNEDLAEILQSSSEFGGGGSGGGGSGGGGSASDLGKK
LLEAARAGQDDEVRILMANGADVNALDTHGVTPLHLAAWRGHLEIVEVLL
KNGADVNAGDVLGRTPLHLAATFGHLEIVEVLLKHGADINAVDTVGVTPL
HLAAGQGHLEIVEVLLKYGADVNAQDKFGKTAFDISIDNGNEDLAEILQS
SS

DLD-6

(SEQ ID NO. 39)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSASDLGKKLLEAARAGQDDEVRILMAN
GADVNAKDTFGETPLHLAAWKGHLEIVEVLLKYGADVNASDLLGRTPLHL
AAWRGHLEIVEVLLKNGADVNASDTGGYTPLHLAAALGHLEIVEVLLKHG
ADVNAQDKFGKTAFDISIDNGNEDLAEILQSSS

DLD-7

(SEQ ID NO. 40)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSGSDLGKKLLEAARAGQDDEVRILMAN
GADVNAVDRAGTTPLHLAAHGGHLEIVEVLLKYGADVNARDLLGRTPLHL
AAWRGHLEIVEVLLKHGADVNASDPLGITPLHLAAATGHLEIVEVLLKNG
ADVNAQDKFGKTAFDISIDNGNEDLAEILQSSS

TABLE 2-continued

DLD-10

(SEQ ID NO. 41)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSGSDLGKKLLEAARAGQDDEVRILMAN
GADVNALDTHGVTPLHLAAWRGHLEIVEVLLKNGADVNAGDVLGRTPLHL
AATFGHLEIVEVLLKHGADINAVDTVGVTPLHLAAGQGHLEIVEVLLKYG
ADVNAQDKFGKTAFDISIDNGNEDLAEILQSSS

DLD-11

(SEQ ID NO. 42)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSASDLGKKLLEAARAGQDDEVRILMAN
GADVNAYDARGVTPLHLAAFSGHLEIVEVLLKNGADVNAIDVIGMTPLHL
AAWIGHLEIVEVLLKHGADVNAVDRSGNTPLHLAAWLGHLEIVEVLLKYG
ADVNAQDKFGKTAFDISIDNGNEDLAEILQSSS

DLD-12

(SEQ ID NO. 43)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDNGNEDLA
EILQSSSEFGGGGSGGGGSGGGGSASDLGKKLLEAARAGQDDEVRILMAN
GADVNATDHLGVTPLHLAAVLGHLEIVEVLLKHGADVNAYDILGRTPLHL
AAWRGHLEIVEVLLKYGADVNAVDTMGETPLHLAAGMGHLEIVEVLLKHG
ADVNAQDKFGKTAFDISIDNGNEDLAEILQSSS

U3D16
(SEQ ID NO. 49)
GSDLGKKLLEAARAGQDDEVRILMANGADVNADDRIGMTPLHLAAIGGHL
EIVEVLLKNGADVNADDVHGRTPLHLAAGRGHLEIVEVLHGADVNAPDRW
GRTPLHLAAHHGHLEIVEVLLKYGADVNAQDKFGKTAFDISIDSGNEDLA
EILQSSSGGGGSGGGGSGGGGSGSDLGKKLLEAARAGQDDEVRILMANGA
DVNAADRYGPTPLHLAAYRGHLEIVEVLLKHGADVNAKDVLGWTPLHLAA
WIGHLEIVEVLLKNGADVNARDRTGETPLHLAAAIGHLEIVEVLLKNGAD
VNAQDKFGKTAFDISIDNGNEDLAEILQSSS

Primer Sequences

Ran2-D-F (SEQ ID NO. 44)
CATGTGCATTATCTGGGATCCGACCTGG

Ran2-D-R (SEQ ID NO. 45)
TAACAGGCCGCAAGCTTTTACGA

Linker-BSAi-D-F (SEQ ID NO. 46)
TTAGCTGGTCTCTGGAGGGAGCGGAGGCGGAGGGAGCGCTAGCGACCTGG
GTAAGAAACTGCTG Linker-BSAi-D-R (SEQ ID NO. 47)
GAAATCCTGCAATCGAGCTCGGAATTCGGAGGCGGAGGGAGCGGAGGCGG
AGTGAGACCTTAGCT Linker Sequence
(GGGGS)x3 Linker (SEQ ID NO. 48)
GGGGSGGGGSGGGGS Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A composition comprising an anti-toxin for treating or protecting against *Clostridium difficile* (*C. difficile*) infections, wherein the anti-toxin comprises a designed ankyrin repeat protein (DARPin) comprising at least one of U3 (SEQ ID NO:13) and 1.4E (SEQ ID NO:2), and wherein the anti-toxin binds to a region on toxin B (TcdB) that is critical for toxin translocation into host cytosol.

2. The composition of claim 1, wherein the composition is formulated to be administered via a mode selected from the group consisting of intravenously, orally, in situ, in situ via engineered commensal bacteria, in situ via engineered commensal yeast, and combinations thereof.

3. The composition of claim 1, wherein the anti-toxin is produced via *Escherichia coli* (*E. coli*) in a fermenter.

4. The composition of claim 1, wherein the anti-toxin comprises DLD-3 (SEQ ID NO. 36), U3D16 (SEQ ID. NO 49), or combinations thereof.

5. The composition of claim 1, wherein the DARPin is a DARPin dimer.

6. The composition of claim 5, wherein the monomeric DARPins are connected by a linker.

7. A method of treating *C. difficile* infection in a subject in need thereof, wherein the method comprises administering to the subject the composition of claim 1.

8. The method of claim 7, wherein the DARPin neutralizes *C. difficile* secreted exotoxins.

9. The method of claim 8, wherein the *C. difficile* secreted exotoxins are toxin B (TcdB).

10. The method of claim 7, wherein the anti-toxin comprises DLD-3 (SEQ ID NO. 36), U3D16 (SEQ ID. NO 49), or combinations thereof.

11. The method of claim 7, wherein the composition is formulated to be administered via a mode selected from the group consisting of intravenously, orally, in situ, in situ via engineered commensal bacteria, in situ via engineered commensal yeast, and combinations thereof.

12. The method of claim 7, wherein the anti-toxin is produced via *E. coli* in a fermenter.

13. A composition comprising an anti-toxin for treating or protecting against *C. difficile* infections, wherein the anti-toxin comprises a designed ankyrin repeat protein (DARPin) comprising both U3 (SEQ ID NO: 13) and 1.4E (SEQ ID NO: 2), and wherein the anti-toxin binds to a region on toxin B (TcdB) that is critical for toxin translocation into host cytosol.

* * * * *

SEQUENCE LISTING

```
<160> NUMBER OF SEQ ID NOS: 49

<210> SEQ ID NO 1
<211> LENGTH: 159
<212> TYPE: PRT
<213> ORGANISM: Artificial Sequence
<220> FEATURE:
<223> OTHER INFORMATION: 1.2E

<400> SEQUENCE: 1

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Tyr Asp Ala Arg Gly Val Thr Pro Leu His Leu Ala Ala Phe Ser Gly
        35                  40                  45

His Leu Glu Ile Val Glu Val Leu Leu Lys Asn Gly Ala Asp Val Asn
    50                  55                  60

Ala Ile Asp Val Ile Gly Met Thr Pro Leu His Leu Ala Ala Trp Ile
65                  70                  75                  80

Gly His Leu Glu Ile Val Glu Val Leu Leu Lys His Gly Ala Asp Val
                85                  90                  95

Asn Ala Val Asp Arg Ser Gly Asn Thr Pro Leu His Leu Ala Ala Trp
            100                 105                 110

Leu Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155

<210> SEQ ID NO 2
<211> LENGTH: 159
<212> TYPE: PRT
<213> ORGANISM: Artificial Sequence
<220> FEATURE:
<223> OTHER INFORMATION: 1.4E

<400> SEQUENCE: 2

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp His Leu Gly Val Thr Pro Leu His Leu Ala Ala Val Leu Gly
        35                  40                  45

His Leu Glu Ile Val Glu Val Leu Leu Lys His Gly Ala Asp Val Asn
    50                  55                  60

Ala Tyr Asp Ile Leu Gly Arg Thr Pro Leu His Leu Ala Ala Trp Arg
65                  70                  75                  80
```

```
Gly His Leu Glu Ile Val Glu Val Leu Leu Lys Tyr Gly Ala Asp Val
                85                  90                  95

Asn Ala Asp Asp Thr Ser Gly Thr Thr Pro Leu His Leu Ala Ala Gly
            100                 105                 110

Glu Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 3
<211> LENGTH: 159
<212> TYPE: PRT
<213> ORGANISM: Artificial Sequence
<220> FEATURE:
<223> OTHER INFORMATION: 1.8H

<400> SEQUENCE: 3

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ile Asp Ala Leu Gly Val Thr Pro Leu His Leu Ala Ala Trp Val Gly
        35                  40                  45

His Leu Glu Ile Val Glu Val Leu Leu Lys Asn Gly Ala Asp Val Asn
    50                  55                  60

Ala Val Asp Val Leu Gly Trp Thr Pro Leu His Leu Ala Ala Trp Lys
65                  70                  75                  80

Gly His Leu Glu Ile Val Glu Val Leu Leu Lys His Gly Ala Asp Val
                85                  90                  95

Asn Ala Met Asp Asn Arg Gly Pro Thr Pro Leu His Leu Ala Ala Val
            100                 105                 110

Asp Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 4
<211> LENGTH: 159
<212> TYPE: PRT
<213> ORGANISM: Artificial Sequence
<220> FEATURE:
<223> OTHER INFORMATION: 1.11E

<400> SEQUENCE: 4

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Thr Asp His Leu Gly Val Thr Pro Leu His Leu Ala Ala Val Leu Gly
        35                  40                  45

His Leu Glu Ile Val Glu Val Leu Leu Lys His Gly Ala Asp Val Asn
    50                  55                  60

Ala Tyr Asp Ile Leu Gly Arg Thr Pro Leu His Leu Ala Ala Trp Arg
```

```
                65                  70                  75                  80

Gly His Leu Glu Ile Val Glu Val Leu Lys Tyr Gly Ala Asp Val
                85                  90                  95

Asn Ala Val Asp Thr Met Gly Glu Thr Pro Leu His Leu Ala Gly
                100                 105                 110

Met Gly His Leu Glu Ile Val Glu Val Leu Leu Lys His Gly Ala Asp
                115                 120                 125

Val Asn Ala Gln Asp Lys Phe Gly Lys Thr Ala Phe Asp Ile Ser Ile
                130                 135                 140

Asp Asn Gly Asn Glu Asp Leu Ala Glu Ile Leu Gln Ser Ser Ser
145                 150                 155

<210> SEQ ID NO 5
<211> LENGTH: 159
<212> TYPE: PRT
<213> ORGANISM: Artificial Sequence
<220> FEATURE:
<223> OTHER INFORMATION: 5.8B

<400> SEQUENCE: 5

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Leu Asp Thr His Gly Val Thr Pro Leu His Leu Ala Ala Trp Arg Gly
                35                  40                  45

His Leu Glu Ile Val Glu Val Leu Leu Lys Asn Gly Ala Asp Val Asn
50                  55                  60

Ala Gly Asp Val Leu Gly Arg Thr Pro Leu His Leu Ala Ala Thr Phe
65                  70                  75                  80

Gly His Leu Glu Ile Val Glu Val Leu Leu Lys His Gly Ala Asp Ile
                85                  90                  95

Asn Ala Val Asp Thr Val Gly Val Thr Pro Leu His Leu Ala Ala Gly
                100                 105                 110

Gln Gly His Leu Glu Ile Val Glu Val Leu Leu Lys Tyr Gly Ala Asp
                115                 120                 125

Val Asn Ala Gln Asp Lys Phe Gly Lys Thr Ala Phe Asp Ile Ser Ile
                130                 135                 140

Asp Asn Gly Asn Glu Asp Leu Ala Glu Ile Leu Gln Ser Ser Ser
145                 150                 155

<210> SEQ ID NO 6
<211> LENGTH: 159
<212> TYPE: PRT
<213> ORGANISM: Artificial Sequence
<220> FEATURE:
<223> OTHER INFORMATION: 5.5A

<400> SEQUENCE: 6

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Val Asp Arg Ala Gly Thr Thr Pro Leu His Leu Ala Ala His Gly Gly
                35                  40                  45

His Leu Glu Ile Val Glu Val Leu Leu Lys Tyr Gly Ala Asp Val Asn
50                  55                  60
```

-continued

Ala Arg Asp Leu Leu Gly Arg Thr Pro Leu His Leu Ala Ala Trp Arg
 65                  70                  75                  80

Gly His Leu Glu Ile Val Glu Val Leu Leu Lys His Gly Ala Asp Val
                 85                  90                  95

Asn Ala Ser Asp Pro Leu Gly Ile Thr Pro Leu His Leu Ala Ala Ala
            100                 105                 110

Thr Gly His Leu Glu Ile Val Glu Val Leu Leu Lys Asn Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155

<210> SEQ ID NO 7
<211> LENGTH: 159
<212> TYPE: PRT
<213> ORGANISM: Artificial Sequence
<220> FEATURE:
<223> OTHER INFORMATION: 7.5A

<400> SEQUENCE: 7

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Leu Asp Thr His Gly Val Thr Pro Leu His Leu Ala Ala Trp Arg Gly
            35                  40                  45

His Leu Glu Ile Val Glu Val Leu Leu Lys Asn Gly Ala Asp Val Asn
        50                  55                  60

Ala Gly Asp Val Leu Gly Arg Thr Pro Leu His Leu Ala Ala Thr Phe
 65                  70                  75                  80

Gly His Leu Glu Ile Val Glu Val Leu Leu Lys His Gly Ala Asp Val
                 85                  90                  95

Asn Ala Val Asp Thr Val Gly Val Thr Pro Leu His Leu Ala Ala Gly
            100                 105                 110

Gln Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155

<210> SEQ ID NO 8
<211> LENGTH: 159
<212> TYPE: PRT
<213> ORGANISM: Artificial Sequence
<220> FEATURE:
<223> OTHER INFORMATION: 5.9C

<400> SEQUENCE: 8

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Gln Asp Tyr Tyr Gly Ser Thr Pro Leu His Leu Ala Ala Trp Leu Gly
            35                  40                  45

His Leu Glu Ile Val Glu Val Leu Leu Lys Asn Gly Ala Asp Val Asn
        50                  55                  60

```
Ala Gly Asp Leu Leu Gly Arg Thr Pro Leu His Leu Ala Ala Trp Phe
 65                  70                  75                  80

Gly His Leu Glu Ile Val Glu Val Leu Leu Lys His Gly Ala Asp Val
                 85                  90                  95

Asn Ala Val Asp Thr Met Gly Glu Thr Pro Leu His Leu Ala Ala Gly
            100                 105                 110

Met Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 9
<211> LENGTH: 159
<212> TYPE: PRT
<213> ORGANISM: Artificial Sequence
<220> FEATURE:
<223> OTHER INFORMATION: 3.11H

<400> SEQUENCE: 9

```
Gly Ser Asp Leu Gly Lys Lys Leu Leu Glu Ala Ala Arg Thr Gly Gln
  1               5                  10                  15

Asp Asp Glu Val Arg Ile Leu Met Ala Asn Gly Ala Asp Val Asn Ala
                 20                  25                  30

Lys Asp Glu Gly Gly Pro Thr Pro Leu His Leu Ala Ala Val Gly Gly
            35                  40                  45

His Leu Glu Ile Val Glu Val Leu Leu Lys His Gly Ala Asp Val Asn
 50                  55                  60

Ala Val Asp Ala Leu Gly Arg Thr Pro Leu His Leu Ala Ala Trp Gln
 65                  70                  75                  80

Gly His Leu Glu Ile Val Glu Val Leu Leu Lys His Gly Ala Asp Val
                 85                  90                  95

Asn Ala Arg Asp Lys Asn Gly Tyr Thr Pro Leu His Leu Ala Ala Gly
            100                 105                 110

Met Gly His Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 10
<211> LENGTH: 159
<212> TYPE: PRT
<213> ORGANISM: Artificial Sequence
<220> FEATURE:
<223> OTHER INFORMATION: 3.5B

<400> SEQUENCE: 10

```
Gly Ser Asp Leu Gly Lys Lys Leu Leu Glu Ala Ala Arg Ala Gly Gln
  1               5                  10                  15

Asp Asp Glu Val Arg Ile Leu Met Ala Asn Gly Ala Asp Val Asn Ala
                 20                  25                  30

Lys Asp Thr Phe Gly Glu Thr Pro Leu His Leu Ala Ala Trp Lys Gly
            35                  40                  45

His Leu Glu Ile Val Glu Val Leu Leu Lys Tyr Gly Ala Asp Val Asn
```

```
                50                  55                  60
Ala Ser Asp Leu Leu Gly Arg Thr Pro Leu His Leu Ala Ala Trp Arg
 65                  70                  75                  80

Gly His Leu Glu Ile Val Glu Val Leu Leu Lys Asn Gly Ala Asp Val
                 85                  90                  95

Asn Ala Ser Asp Thr Gly Gly Tyr Thr Pro Leu His Leu Ala Ala Ala
                100                 105                 110

Leu Gly His Leu Glu Ile Val Glu Val Leu Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 11
<211> LENGTH: 159
<212> TYPE: PRT
<213> ORGANISM: Artificial Sequence
<220> FEATURE:
<223> OTHER INFORMATION: 8.1B

<400> SEQUENCE: 11

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Lys Asp Gly Ser Gly Val Thr Pro Leu His Leu Ala Ala Val Ala Gly
             35                  40                  45

His Leu Glu Ile Val Glu Val Leu Leu Lys Asn Gly Ala Asp Val Asn
         50                  55                  60

Ala Arg Asp Arg Leu Gly Arg Thr Pro Leu His Leu Ala Ala Trp Arg
 65                  70                  75                  80

Gly His Leu Glu Ile Val Glu Val Leu Leu Lys Asn Gly Ala Asp Val
                 85                  90                  95

Asn Ala Lys Asp Leu Gly Gly Asp Thr Pro Leu His Leu Ala Ala Ala
                100                 105                 110

Leu Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 12
<211> LENGTH: 158
<212> TYPE: PRT
<213> ORGANISM: Artificial Sequence
<220> FEATURE:
<223> OTHER INFORMATION: 3.9G

<400> SEQUENCE: 12

Gly Ser Asp Leu Gly Lys Leu Leu Glu Ala Ala Arg Ala Gly Gln Asp
 1               5                  10                  15

Asp Glu Val Arg Ile Leu Met Ala Asn Gly Ala Asp Val Asn Ala Asn
                 20                  25                  30

Asp Arg Arg Gly Ile Thr Pro Leu His Leu Ala Ala Ile Asn Gly His
             35                  40                  45
```

```
Leu Glu Ile Val Glu Val Leu Leu Lys Asn Gly Ala Asp Val Asn Ala
 50                  55                  60

Val Asp Val Leu Gly Phe Thr Pro Leu His Leu Ala Ala Trp Arg Gly
 65                  70                  75                  80

His Leu Glu Ile Val Glu Val Leu Leu Lys Asn Gly Ala Asp Val Asn
                 85                  90                  95

Ala Phe Asp Lys Ser Gly Ser Thr Pro Leu His Leu Ala Ala His Phe
                100                 105                 110

Gly His Leu Glu Ile Val Glu Val Leu Leu Lys Tyr Gly Ala Asp Val
                115                 120                 125

Asn Ala Gln Asp Lys Phe Gly Lys Thr Ala Phe Asp Ile Ser Ile Asp
130                 135                 140

Asn Gly Asn Glu Asp Leu Ala Glu Ile Leu Gln Ser Ser Ser
145                 150                 155

<210> SEQ ID NO 13
<211> LENGTH: 157
<212> TYPE: PRT
<213> ORGANISM: Artificial Sequence
<220> FEATURE:
<223> OTHER INFORMATION: U3

<400> SEQUENCE: 13

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Asp Asp Arg Ile Gly Met Thr Pro Leu His Leu Ala Ala Ile Gly Gly
                 35                  40                  45

His Leu Glu Ile Val Glu Val Leu Leu Lys Asn Gly Ala Asp Val Asn
 50                  55                  60

Ala Asp Asp Val His Gly Arg Thr Pro Leu His Leu Ala Ala Gly Arg
 65                  70                  75                  80

Gly His Leu Glu Ile Val Glu Val Leu His Gly Ala Asp Val Asn Ala
                 85                  90                  95

Pro Asp Arg Trp Gly Arg Thr Pro Leu His Leu Ala Ala His His Gly
                100                 105                 110

His Leu Glu Ile Val Glu Val Leu Leu Lys Tyr Gly Ala Asp Val Asn
                115                 120                 125

Ala Gln Asp Lys Phe Gly Lys Thr Ala Phe Asp Ile Ser Ile Asp Ser
                130                 135                 140

Gly Asn Glu Asp Leu Ala Glu Ile Leu Gln Ser Ser Ser
145                 150                 155

<210> SEQ ID NO 14
<211> LENGTH: 126
<212> TYPE: PRT
<213> ORGANISM: Artificial Sequence
<220> FEATURE:
<223> OTHER INFORMATION: U5

<400> SEQUENCE: 14

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Asp Asp Arg Ile Gly Met Thr Pro Leu His Leu Ala Ala Ile Gly Gly
                 35                  40                  45
```

His Leu Glu Ile Val Glu Val Leu Leu Lys Asn Gly Ala Asp Val Asn
            50                  55                  60

Ala Asp Asp Val His Gly Arg Thr Pro Leu His Leu Ala Ala Gly Arg
65                  70                  75                  80

Gly His Leu Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Ser Ser Ser
            115                 120                 125

<210> SEQ ID NO 15
<211> LENGTH: 159
<212> TYPE: PRT
<213> ORGANISM: Artificial Sequence
<220> FEATURE:
<223> OTHER INFORMATION: TEMP

<400> SEQUENCE: 15

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Asn Asp Arg Arg Gly Ile Thr Pro Leu His Leu Ala Ala Ile Asn Gly
            35                  40                  45

His Leu Glu Ile Val Glu Val Leu Leu Lys Asn Gly Ala Asp Val Asn
            50                  55                  60

Ala Val Asp Val Leu Gly Phe Thr Pro Leu His Leu Ala Ala Trp Arg
65                  70                  75                  80

Gly His Leu Glu Ile Val Glu Val Leu Leu Lys Asn Gly Ala Asp Val
                85                  90                  95

Asn Ala Phe Asp Lys Ser Gly Ser Thr Pro Leu His Leu Ala Ala His
                100                 105                 110

Phe Gly His Leu Glu Ile Val Glu Val Leu Leu Lys Tyr Gly Ala Asp
            115                 120                 125

Val Asn Ala Gln Asp Lys Phe Gly Lys Thr Ala Phe Asp Ile Ser Ile
            130                 135                 140

Asp Asn Gly Asn Glu Asp Leu Ala Glu Ile Leu Gln Ser Ser Ser
145                 150                 155

<210> SEQ ID NO 16
<211> LENGTH: 159
<212> TYPE: PRT
<213> ORGANISM: Artificial Sequence
<220> FEATURE:
<223> OTHER INFORMATION: D3

<400> SEQUENCE: 16

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
            50                  55                  60

Ala Lys Asp Val Leu Gly Trp Thr Pro Leu His Leu Ala Ala Trp Ile

```
                65                  70                  75                  80
Gly His Leu Glu Ile Val Glu Val Leu Leu Lys Asn Gly Ala Asp Val
                    85                  90                  95

Asn Ala Val Asp Val Thr Gly Glu Thr Pro Leu His Leu Ala Ala Val
                100                 105                 110

Met Gly His Leu Glu Ile Val Glu Val Leu Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 17
<211> LENGTH: 159
<212> TYPE: PRT
<213> ORGANISM: Artificial Sequence
<220> FEATURE:
<223> OTHER INFORMATION: D10

<400> SEQUENCE: 17

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
        50                  55                  60

Ala Lys Asp Val Leu Gly Trp Thr Pro Leu His Leu Ala Ala Trp Ile
65                  70                  75                  80

Gly His Leu Glu Ile Val Glu Val Leu Leu Lys Asn Gly Ala Asp Val
                    85                  90                  95

Asn Ala Val Asp Val Thr Gly Glu Thr Pro Leu His Leu Ala Ala Val
                100                 105                 110

Met Gly His Leu Glu Ile Ala Glu Val Leu Leu Lys His Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 18
<211> LENGTH: 159
<212> TYPE: PRT
<213> ORGANISM: Artificial Sequence
<220> FEATURE:
<223> OTHER INFORMATION: D13

<400> SEQUENCE: 18

Gly Ser Asp Leu Gly Lys Lys Leu Leu Glu Ala Ala Arg Ala Gly Gln
1               5                   10                  15

Asp Asp Glu Val Arg Ile Leu Val Ala Asn Gly Ala Asp Val Asn Ala
                20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
        50                  55                  60
```

```
Ala Lys Asp Val Leu Gly Trp Thr Pro Leu His Leu Ala Ala Trp Ile
 65                  70                  75                  80

Gly His Leu Glu Ile Val Glu Val Leu Leu Lys Asn Gly Ala Asp Val
             85                  90                  95

Asn Ala Val Asp Val Thr Gly Glu Thr Pro Leu His Leu Ala Ala Val
            100                 105                 110

Met Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 19
<211> LENGTH: 159
<212> TYPE: PRT
<213> ORGANISM: Artificial Sequence
<220> FEATURE:
<223> OTHER INFORMATION: D7

<400> SEQUENCE: 19

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Arg Tyr Gly Pro Thr Pro Leu His Leu Ala Ala Tyr Arg Gly
        35                  40                  45

His Leu Glu Ile Val Glu Val Leu Leu Lys His Gly Ala Asp Val Asn
    50                  55                  60

Ala Lys Asp Val Leu Gly Trp Thr Pro Leu His Leu Ala Ala Trp Ile
 65                  70                  75                  80

Gly His Pro Glu Ile Val Glu Val Leu Leu Lys Asn Gly Ala Asp Val
             85                  90                  95

Asn Ala Val Asp Val Thr Gly Glu Thr Pro Leu His Leu Ala Ala Val
            100                 105                 110

Met Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 20
<211> LENGTH: 159
<212> TYPE: PRT
<213> ORGANISM: Artificial Sequence
<220> FEATURE:
<223> OTHER INFORMATION: D9

<400> SEQUENCE: 20

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Arg Tyr Gly Pro Thr Pro Leu His Leu Ala Ala Tyr Arg Gly
        35                  40                  45

His Leu Glu Ile Ala Glu Val Leu Leu Lys His Gly Ala Asp Val Asn
    50                  55                  60
```

```
Ala Lys Asp Val Leu Gly Trp Thr Pro Leu His Leu Ala Ala Trp Ile
 65                  70                  75                  80

Gly His Leu Glu Ile Val Glu Val Leu Leu Lys Asn Gly Ala Asp Val
                 85                  90                  95

Asn Ala Val Asp Val Thr Gly Glu Thr Pro Leu His Leu Ala Ala Val
            100                 105                 110

Met Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 21
<211> LENGTH: 159
<212> TYPE: PRT
<213> ORGANISM: Artificial Sequence
<220> FEATURE:
<223> OTHER INFORMATION: D6

<400> SEQUENCE: 21

```
Gly Ser Asp Leu Gly Lys Lys Leu Leu Glu Ala Ala Arg Ala Gly Gln
  1               5                  10                  15

Asp Asp Glu Val Arg Ile Leu Met Ala Asn Gly Ala Asp Val Asn Ala
                 20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
 50                  55                  60

Ala Lys Asp Val Leu Gly Trp Thr Pro Leu His Leu Ala Ala Trp Ile
 65                  70                  75                  80

Gly His Leu Glu Ile Val Glu Val Leu Pro Lys Asn Gly Ala Asp Val
                 85                  90                  95

Asn Ala Val Asp Val Thr Gly Glu Thr Pro Leu His Leu Ala Ala Val
            100                 105                 110

Met Gly His Leu Glu Ile Val Glu Val Leu Leu Lys His Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 22
<211> LENGTH: 159
<212> TYPE: PRT
<213> ORGANISM: Artificial Sequence
<220> FEATURE:
<223> OTHER INFORMATION: D15

<400> SEQUENCE: 22

```
Gly Ser Asp Leu Gly Lys Lys Leu Leu Glu Ala Ala Arg Ala Gly Gln
  1               5                  10                  15

Asp Asp Glu Val Arg Ile Leu Met Ala Asn Gly Ala Asp Val Asn Ala
                 20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
```

```
               50                  55                  60
Ala Lys Asp Val Leu Gly Trp Thr Pro Leu His Leu Ala Ala Trp Ile
 65                  70                  75                  80

Gly His Leu Glu Ile Val Glu Val Leu Leu Lys Asn Gly Ala Asp Val
                 85                  90                  95

Asn Ala Val Asp Val Thr Gly Glu Thr Pro Leu His Leu Ala Ala Val
                100                 105                 110

Met Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 23
<211> LENGTH: 159
<212> TYPE: PRT
<213> ORGANISM: Artificial Sequence
<220> FEATURE:
<223> OTHER INFORMATION: D16

<400> SEQUENCE: 23

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                20                  25                  30

Ala Asp Arg Tyr Gly Pro Thr Pro Leu His Leu Ala Ala Tyr Arg Gly
            35                  40                  45

His Leu Glu Ile Val Glu Val Leu Leu Lys His Gly Ala Asp Val Asn
        50                  55                  60

Ala Lys Asp Val Leu Gly Trp Thr Pro Leu His Leu Ala Ala Trp Ile
 65                  70                  75                  80

Gly His Leu Glu Ile Val Glu Val Leu Leu Lys Asn Gly Ala Asp Val
                 85                  90                  95

Asn Ala Arg Asp Arg Thr Gly Glu Thr Pro Leu His Leu Ala Ala Ala
                100                 105                 110

Ile Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155

<210> SEQ ID NO 24
<211> LENGTH: 159
<212> TYPE: PRT
<213> ORGANISM: Artificial Sequence
<220> FEATURE:
<223> OTHER INFORMATION: D8

<400> SEQUENCE: 24

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                20                  25                  30

Ala Asp Arg Tyr Gly Pro Thr Pro Leu His Leu Ala Ala Tyr Arg Gly
            35                  40                  45
```

```
His Leu Glu Ile Val Glu Val Leu Leu Lys His Gly Ala Asp Val Asn
    50                  55                  60

Ala Lys Asp Leu Leu Gly Phe Thr Pro Val His Leu Ala Ala Trp Leu
65                  70                  75                  80

Gly His Leu Glu Ile Val Glu Val Leu Leu Lys Asn Gly Ala Asp Val
                85                  90                  95

Asn Ala Arg Asp Arg Thr Gly Glu Thr Pro Leu His Leu Ala Ala Ala
            100                 105                 110

Ile Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 25
<211> LENGTH: 159
<212> TYPE: PRT
<213> ORGANISM: Artificial Sequence
<220> FEATURE:
<223> OTHER INFORMATION: D14

<400> SEQUENCE: 25

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Leu Asp Val Arg Gly Ser Thr Pro Leu His Leu Ala Ala Phe Lys Gly
            35                  40                  45

His Leu Glu Ile Val Glu Val Leu Leu Lys Asn Gly Ala Asp Val Asn
    50                  55                  60

Ala Lys Asp Leu Leu Gly Phe Thr Pro Val His Leu Ala Ala Trp Leu
65                  70                  75                  80

Gly His Leu Glu Ile Val Glu Val Leu Leu Lys Asn Gly Ala Asp Val
                85                  90                  95

Asn Ala Gly Asp Arg Thr Gly Glu Thr Pro Leu His Leu Ala Ala Ala
            100                 105                 110

Ile Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155
```

<210> SEQ ID NO 26
<211> LENGTH: 159
<212> TYPE: PRT
<213> ORGANISM: Artificial Sequence
<220> FEATURE:
<223> OTHER INFORMATION: D1

<400> SEQUENCE: 26

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Leu Asp Val Arg Gly Ser Thr Pro Leu His Leu Ala Ala Phe Lys Gly
            35                  40                  45
```

His Leu Glu Ile Val Glu Val Leu Leu Lys Asn Gly Ala Asp Val Asn
    50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Pro Lys Asn Gly Ala Asp Val
                 85                  90                  95

Asn Ala Arg Asp Arg Thr Gly Glu Thr Pro Leu His Leu Ala Ala Ala
            100                 105                 110

Ile Gly His Leu Glu Ile Val Glu Ile Leu Leu Lys Tyr Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155

<210> SEQ ID NO 27
<211> LENGTH: 159
<212> TYPE: PRT
<213> ORGANISM: Artificial Sequence
<220> FEATURE:
<223> OTHER INFORMATION: D2

<400> SEQUENCE: 27

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Leu Asp Val Arg Gly Ser Thr Pro Leu His Leu Ala Ala Phe Lys Gly
        35                  40                  45

His Leu Glu Ile Val Glu Val Leu Leu Lys Asn Gly Ala Asp Val Asn
    50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Leu Lys Asn Gly Ala Asp Val
                 85                  90                  95

Asn Ala Arg Asp Arg Thr Gly Glu Thr Pro Leu His Leu Ala Ala Ala
            100                 105                 110

Ile Gly His Leu Glu Ile Val Glu Val Leu Leu Lys Asn Gly Ala Asp
            115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Ser Ser Ser
145                 150                 155

<210> SEQ ID NO 28
<211> LENGTH: 159
<212> TYPE: PRT
<213> ORGANISM: Artificial Sequence
<220> FEATURE:
<223> OTHER INFORMATION: D4

<400> SEQUENCE: 28

Gly Ser Asp Leu Gly Lys Lys Leu Leu Glu Ala Ala Arg Ala Gly Gln
1               5                   10                  15

Asp Gly Glu Val Arg Ile Leu Met Ala Asn Gly Ala Asp Val Asn Ala
            20                  25                  30

Leu Asp Val Arg Gly Ser Thr Pro Leu His Leu Ala Ala Phe Lys Gly

```
                35                  40                  45
His Leu Glu Ile Val Glu Val Leu Leu Lys Asn Gly Ala Asp Val Asn
 50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Leu Lys Asn Gly Ala Asp Val
                 85                  90                  95

Asn Ala Arg Asp Arg Thr Gly Glu Thr Pro Leu His Leu Ala Ala Ala
                100                 105                 110

Ile Gly His Leu Glu Ile Val Glu Val Leu Leu Lys Asn Gly Ala Asp
                115                 120                 125

Val Asn Ala Gln Asp Lys Phe Gly Lys Thr Ala Phe Asp Ile Ser Ile
                130                 135                 140

Asp Asn Gly Asn Glu Asp Leu Ala Glu Ile Leu Gln Ser Ser Ser
145                 150                 155
```

<210> SEQ ID NO 29
<211> LENGTH: 159
<212> TYPE: PRT
<213> ORGANISM: Artificial Sequence
<220> FEATURE:
<223> OTHER INFORMATION: D12

<400> SEQUENCE: 29

```
Gly Ser Asp Leu Gly Lys Lys Leu Leu Glu Ala Ala Arg Ala Gly Gln
 1               5                  10                  15

Asp Asp Glu Val His Ile Leu Met Ala Asn Gly Ala Asp Val Asn Ala
                 20                  25                  30

Leu Asp Val Arg Gly Ser Thr Pro Leu His Leu Ala Ala Phe Lys Gly
                 35                  40                  45

His Leu Glu Ile Val Glu Val Leu Leu Lys Asn Gly Ala Asp Val Asn
 50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Leu Lys Asn Gly Ala Asp Val
                 85                  90                  95

Asn Ala Arg Asp Arg Thr Gly Glu Thr Pro Leu His Leu Ala Ala Ala
                100                 105                 110

Ile Gly His Leu Glu Ile Val Glu Val Leu Leu Lys Asn Gly Ala Asp
                115                 120                 125

Val Asn Ala Gln Asp Lys Phe Gly Lys Thr Ala Phe Asp Ile Ser Ile
                130                 135                 140

Asp Asn Gly Asn Glu Asp Leu Ala Glu Ile Leu Gln Ser Ser Ser
145                 150                 155
```

<210> SEQ ID NO 30
<211> LENGTH: 159
<212> TYPE: PRT
<213> ORGANISM: Artificial Sequence
<220> FEATURE:
<223> OTHER INFORMATION: D5

<400> SEQUENCE: 30

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30
```

```
Leu Asp Val Arg Gly Ser Thr Pro Leu His Leu Ala Ala Phe Lys Gly
         35                  40                  45

His Leu Glu Ile Val Glu Val Leu Leu Lys Asn Gly Ala Asp Val Asp
 50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Leu Lys Asn Gly Ala Asp Val
                 85                  90                  95

Asn Ala Arg Asp Arg Thr Gly Glu Thr Pro Leu His Leu Ala Ala Ala
                100                 105                 110

Ile Gly His Leu Glu Ile Val Glu Val Leu Leu Lys Asn Gly Ala Asp
                115                 120                 125

Val Asn Ala Gln Asp Lys Phe Gly Lys Thr Ala Ser Asp Ile Ser Ile
        130                 135                 140

Asp Asn Gly Asn Glu Asp Leu Ala Glu Ile Leu Gln Ser Ser Ser
145                 150                 155
```

<210> SEQ ID NO 31
<211> LENGTH: 159
<212> TYPE: PRT
<213> ORGANISM: Artificial Sequence
<220> FEATURE:
<223> OTHER INFORMATION: D11

<400> SEQUENCE: 31

```
Gly Ser Asp Leu Gly Lys Lys Leu Leu Glu Ala Gly Arg Ala Gly Gln
 1               5                  10                  15

Asp Asp Glu Val Arg Ile Leu Met Ala Asn Gly Ala Asp Val Asn Ala
                 20                  25                  30

Leu Asp Val Arg Gly Ser Thr Pro Leu His Leu Ala Ala Phe Lys Gly
         35                  40                  45

His Leu Glu Ile Val Glu Val Leu Leu Lys Asn Gly Ala Asp Val Asn
 50                  55                  60

Ala Lys Asp Leu Leu Gly Phe Thr Pro Val His Leu Ala Ala Trp Leu
 65                  70                  75                  80

Gly His Leu Glu Ile Val Glu Val Leu Leu Arg Asn Gly Ala Asp Val
                 85                  90                  95

Asn Ala Arg Asp Arg Thr Gly Glu Thr Pro Leu His Leu Ala Ala Ala
                100                 105                 110

Ile Gly His Leu Glu Ile Val Glu Val Leu Leu Lys Asn Gly Ala Asp
                115                 120                 125

Val Asn Ala Gln Asp Lys Phe Gly Lys Thr Ala Phe Asp Ile Ser Ile
        130                 135                 140

Asp Asn Gly Asn Glu Asp Leu Ala Glu Ile Leu Gln Ser Ser Ser
145                 150                 155
```

<210> SEQ ID NO 32
<211> LENGTH: 159
<212> TYPE: PRT
<213> ORGANISM: Artificial Sequence
<220> FEATURE:
<223> OTHER INFORMATION: 1.4E T10-2

<400> SEQUENCE: 32

```
Gly Ser Asp Leu Gly Gly Leu Leu Glu Ala Ala Gln Ala Gly Gln
 1               5                  10                  15

Asp Asp Glu Val His Ile Leu Met Ala Asn Gly Ala Asp Val Asn Thr
                 20                  25                  30
```

Thr Asp His Leu Gly Val Thr Pro Leu His Leu Ala Ala Val Leu Gly
        35                  40                  45

His Leu Glu Ile Val Glu Val Leu Leu Gln His Gly Ala Asp Val Asn
    50                  55                  60

Ala Tyr Asp Ile Leu Gly Arg Thr Pro Leu His Leu Ala Ala Trp Lys
65                  70                  75                  80

Gly His Leu Glu Ile Val Glu Val Leu Leu Gln Tyr Gly Ala Asp Val
                85                  90                  95

Asn Ala Asp Asp Thr Ser Gly Thr Thr Pro Leu His Leu Ala Ala Ala
            100                 105                 110

Glu Gly His Leu Glu Ile Val Glu Val Leu Leu Gln Tyr Gly Ala Asp
        115                 120                 125

Val Asn Ala Gln Asp Ile Phe Gly Thr Ala Ser Asp Ile Ser Ile
    130                 135                 140

Asp Asn Gly Asn Glu Asp Leu Ala Glu Ile Leu Gln Ser Ser Ser
145                 150                 155

<210> SEQ ID NO 33
<211> LENGTH: 159
<212> TYPE: PRT
<213> ORGANISM: Artificial Sequence
<220> FEATURE:
<223> OTHER INFORMATION: 1.4E C3

<400> SEQUENCE: 33

Gly Ser Asp Leu Gly Glu Leu Leu Glu Ala Ala Gln Ala Gly Gln
1               5                   10                  15

Asp Asp Glu Val His Ile Leu Met Ala Asn Gly Ala Asp Val Asn Ala
            20                  25                  30

Thr Asn His Leu Gly Val Thr Pro Leu His Leu Ala Ala Val Leu Gly
        35                  40                  45

His Leu Glu Ile Val Glu Val Leu Leu Gln His Gly Ala Asp Val Asn
    50                  55                  60

Ala Ile Asp Ile Leu Gly Arg Thr Pro Leu His Leu Ala Ala Trp Lys
65                  70                  75                  80

Gly His Leu Glu Ile Val Glu Val Leu Leu Gln His Gly Ala Asp Val
                85                  90                  95

Asn Ala Asp Asp Thr Ser Gly Thr Thr Pro Leu His Leu Ala Ala Gly
            100                 105                 110

Glu Gly His Leu Glu Ile Val Glu Val Leu Leu Gln His Gly Ala Asp
        115                 120                 125

Val Asn Ala Gln Asp Ile Asn Gly Thr Thr Ala Ser Asp Ile Ser Ile
    130                 135                 140

Asp Asn Gly Asn Glu Asp Leu Ala Glu Ile Leu Gln Ser Ser Ser
145                 150                 155

<210> SEQ ID NO 34
<211> LENGTH: 335
<212> TYPE: PRT
<213> ORGANISM: Artificial Sequence
<220> FEATURE:
<223> OTHER INFORMATION: DLD-1

<400> SEQUENCE: 34

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala

```
            20                  25                  30
Val Asp Arg Ala Gly Thr Thr Pro Leu His Leu Ala Ala His Gly Gly
             35                  40                  45
His Leu Glu Ile Val Glu Val Leu Leu Lys Tyr Gly Ala Asp Val Asn
         50                  55                  60
Ala Arg Asp Leu Leu Gly Arg Thr Pro Leu His Leu Ala Ala Trp Arg
 65                  70                  75                  80
Gly His Leu Glu Ile Val Glu Val Leu Lys His Gly Ala Asp Val
                 85                  90                  95
Asn Ala Ser Asp Pro Leu Gly Ile Thr Pro Leu His Leu Ala Ala
             100                 105                 110
Thr Gly His Leu Glu Ile Val Glu Val Leu Leu Lys Asn Gly Ala Asp
             115                 120                 125
Val Asn Ala Gln Asp Lys Phe Gly Lys Thr Ala Phe Asp Ile Ser Ile
             130                 135                 140
Asp Asn Gly Asn Glu Asp Leu Ala Glu Ile Leu Gln Ser Ser Ser Glu
145                 150                 155                 160
Phe Gly Gly Gly Gly Ser Gly Gly Gly Ser Gly Gly Gly Gly Ser
                 165                 170                 175
Ala Ser Asp Leu Gly Lys Lys Leu Leu Glu Ala Ala Arg Ala Gly Gln
             180                 185                 190
Asp Asp Gly Val Arg Ile Leu Met Ala Asn Gly Ala Asp Val Asn Ala
             195                 200                 205
Leu Asp Thr His Gly Val Thr Pro Leu His Leu Ala Ala Trp Arg Gly
             210                 215                 220
His Leu Glu Ile Val Glu Val Leu Leu Lys Asn Gly Ala Asp Val Asn
225                 230                 235                 240
Ala Gly Asp Val Leu Gly Arg Thr Pro Leu His Leu Ala Ala Thr Phe
             245                 250                 255
Gly His Leu Glu Ile Val Glu Val Leu Leu Lys His Gly Ala Asp Val
             260                 265                 270
Asn Ala Val Asp Thr Val Gly Val Thr Pro Leu His Leu Ala Ala Gly
             275                 280                 285
Gln Gly His Leu Glu Ile Val Glu Val Leu Leu Lys Tyr Gly Ala Asp
             290                 295                 300
Val Asn Ala Gln Asp Lys Phe Gly Lys Thr Ala Phe Asp Ile Ser Ile
305                 310                 315                 320
Asp Asn Gly Asn Glu Asp Leu Ala Glu Ile Leu Gln Ser Ser Ser
                 325                 330                 335

<210> SEQ ID NO 35
<211> LENGTH: 335
<212> TYPE: PRT
<213> ORGANISM: Artificial Sequence
<220> FEATURE:
<223> OTHER INFORMATION: DLD-2

<400> SEQUENCE: 35

Gly Ser Asp Leu Gly Lys Lys Leu Leu Glu Ala Ala Arg Ala Gly Gln
1               5                  10                  15
Asp Asp Glu Val Arg Ile Leu Met Ala Asn Gly Ala Asp Val Asn Ala
                 20                  25                  30
Ile Asp Ala Leu Gly Val Thr Pro Leu His Leu Ala Ala Trp Val Gly
             35                  40                  45
His Leu Glu Ile Val Glu Val Leu Leu Lys Asn Gly Ala Asp Val Asn
```

```
            50                  55                  60
Ala Val Asp Val Leu Gly Trp Thr Pro Leu His Leu Ala Ala Trp Lys
 65                  70                  75                  80

Gly His Leu Glu Ile Val Glu Val Leu Leu Lys His Gly Ala Asp Val
                 85                  90                  95

Asn Ala Met Asp Asn Arg Gly Pro Thr Pro Leu His Leu Ala Ala Val
                100                 105                 110

Asp Gly His Leu Glu Ile Val Glu Val Leu Leu Lys Asn Gly Ala Asp
                115                 120                 125

Val Asn Ala Gln Asp Lys Phe Gly Lys Thr Ala Phe Asp Ile Ser Ile
130                 135                 140

Asp Asn Gly Asn Glu Asp Leu Ala Glu Ile Leu Gln Ser Ser Ser Glu
145                 150                 155                 160

Phe Gly Gly Gly Gly Ser Gly Gly Gly Ser Gly Gly Gly Gly Ser
                165                 170                 175

Ala Ser Asp Leu Gly Lys Lys Leu Leu Glu Ala Ala Arg Ala Gly Gln
                180                 185                 190

Asp Asp Glu Val Arg Ile Leu Met Ala Asn Gly Ala Asp Val Asn Ala
                195                 200                 205

Tyr Asp Ala Arg Gly Val Thr Pro Leu His Leu Ala Ala Phe Ser Gly
210                 215                 220

His Leu Glu Ile Val Glu Val Leu Leu Lys Asn Gly Ala Asp Val Asn
225                 230                 235                 240

Ala Ile Asp Val Ile Gly Met Thr Pro Leu His Leu Ala Ala Trp Ile
                245                 250                 255

Gly His Leu Glu Ile Val Glu Val Leu Leu Lys His Gly Ala Asp Val
                260                 265                 270

Asn Ala Val Asp Arg Ser Gly Asn Thr Pro Leu His Leu Ala Ala Trp
                275                 280                 285

Leu Gly His Leu Glu Ile Val Glu Val Leu Leu Lys Tyr Gly Ala Asp
290                 295                 300

Val Asn Ala Gln Asp Lys Phe Gly Lys Thr Ala Phe Asp Ile Ser Ile
305                 310                 315                 320

Asp Asn Gly Asn Glu Asp Leu Ala Glu Ile Leu Gln Ser Ser Ser
                325                 330                 335

<210> SEQ ID NO 36
<211> LENGTH: 333
<212> TYPE: PRT
<213> ORGANISM: Artificial Sequence
<220> FEATURE:
<223> OTHER INFORMATION: DLD-3

<400> SEQUENCE: 36

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                20                  25                  30

Asp Asp Arg Ile Gly Met Thr Pro Leu His Leu Ala Ala Ile Gly Gly
             35                  40                  45

His Leu Glu Ile Val Glu Val Leu Leu Lys Asn Gly Ala Asp Val Asn
          50                  55                  60

Ala Asp Asp Val His Gly Arg Thr Pro Leu His Leu Ala Ala Gly Arg
 65                  70                  75                  80

Gly His Leu Glu Ile Val Glu Val Leu His Gly Ala Asp Val Asn Ala
```

85                  90                  95
Pro Asp Arg Trp Gly Arg Thr Pro Leu His Leu Ala Ala His His Gly
                100                 105                 110
His Leu Glu Ile Val Glu Val Leu Leu Lys Tyr Gly Ala Asp Val Asn
            115                 120                 125
Ala Gln Asp Lys Phe Gly Lys Thr Ala Phe Asp Ile Ser Ile Asp Ser
        130                 135                 140
Gly Asn Glu Asp Leu Ala Glu Ile Leu Gln Ser Ser Ser Glu Phe Gly
145                 150                 155                 160
Gly Gly Gly Ser Gly Gly Gly Ser Gly Gly Gly Ser Ala Ser
                165                 170                 175
Asp Leu Gly Lys Lys Leu Leu Glu Ala Ala Arg Ala Gly Gln Asp Asp
                180                 185                 190
Glu Val Arg Ile Leu Met Ala Asn Gly Ala Asp Val Asn Ala Gln Asp
            195                 200                 205
Tyr Tyr Gly Ser Thr Pro Leu His Leu Ala Ala Trp Leu Gly His Leu
        210                 215                 220
Glu Ile Val Glu Val Leu Leu Lys Asn Gly Ala Asp Val Asn Ala Gly
225                 230                 235                 240
Asp Leu Leu Gly Arg Thr Pro Leu His Leu Ala Ala Trp Phe Gly His
                245                 250                 255
Leu Glu Ile Val Glu Val Leu Leu Lys His Gly Ala Asp Val Asn Ala
            260                 265                 270
Val Asp Thr Met Gly Glu Thr Pro Leu His Leu Ala Ala Gly Met Gly
        275                 280                 285
His Leu Glu Ile Val Glu Val Leu Leu Lys His Gly Ala Asp Val Asn
    290                 295                 300
Ala Gln Asp Lys Phe Gly Lys Thr Ala Phe Asp Ile Ser Ile Asp Asn
305                 310                 315                 320
Gly Asn Glu Asp Leu Ala Glu Ile Leu Gln Ser Ser Ser
                325                 330

<210> SEQ ID NO 37
<211> LENGTH: 333
<212> TYPE: PRT
<213> ORGANISM: Artificial Sequence
<220> FEATURE:
<223> OTHER INFORMATION: DLD-4

<400> SEQUENCE: 37

Gly Ser Asp Leu Gly Lys Lys Leu Leu Glu Ala Ala Arg Ala Gly Gln
1               5                   10                  15
Asp Asp Glu Val Arg Ile Leu Met Ala Asn Gly Ala Asp Val Asn Ala
            20                  25                  30
Asp Asp Arg Ile Gly Met Thr Pro Leu His Leu Ala Ala Ile Gly Gly
        35                  40                  45
His Leu Glu Ile Val Glu Val Leu Leu Lys Asn Gly Ala Asp Val Asn
    50                  55                  60
Ala Asp Asp Val His Gly Arg Thr Pro Leu His Leu Ala Ala Gly Arg
65                  70                  75                  80
Gly His Leu Glu Ile Val Glu Val Leu His Gly Ala Asp Val Asn Ala
                85                  90                  95
Pro Asp Arg Trp Gly Arg Thr Pro Leu His Leu Ala Ala His His Gly
                100                 105                 110
His Leu Glu Ile Val Glu Val Leu Leu Lys Tyr Gly Ala Asp Val Asn

```
            115                 120                 125
Ala Gln Asp Lys Phe Gly Lys Thr Ala Phe Asp Ile Ser Ile Asp Asn
130                 135                 140

Gly Asn Glu Asp Leu Ala Glu Ile Leu Gln Ser Ser Ser Glu Phe Gly
145                 150                 155                 160

Gly Gly Gly Ser Gly Gly Gly Ser Gly Gly Gly Ser Ala Ser
                165                 170                 175

Asp Leu Gly Lys Lys Leu Leu Glu Ala Ala Arg Ala Gly Gln Asp Asp
            180                 185                 190

Glu Val Arg Ile Leu Met Ala Asn Gly Ala Asp Val Asn Ala Thr Asp
        195                 200                 205

His Leu Gly Val Thr Pro Leu His Leu Ala Ala Val Leu Gly His Leu
    210                 215                 220

Glu Ile Val Glu Val Leu Leu Lys His Gly Ala Asp Val Asn Ala Tyr
225                 230                 235                 240

Asp Ile Leu Gly Arg Thr Pro Leu His Leu Ala Ala Trp Arg Gly His
                245                 250                 255

Leu Glu Ile Val Glu Val Leu Leu Lys Tyr Gly Ala Asp Val Asn Ala
            260                 265                 270

Asp Asp Thr Ser Gly Thr Thr Pro Leu His Leu Ala Ala Gly Glu Gly
        275                 280                 285

His Leu Glu Ile Val Glu Val Leu Leu Lys Tyr Gly Ala Asp Val Asn
    290                 295                 300

Ala Gln Asp Lys Phe Gly Lys Thr Ala Phe Asp Ile Ser Ile Asp Asn
305                 310                 315                 320

Gly Asn Glu Asp Leu Ala Glu Ile Leu Gln Ser Ser Ser
                325                 330

<210> SEQ ID NO 38
<211> LENGTH: 302
<212> TYPE: PRT
<213> ORGANISM: Artificial Sequence
<220> FEATURE:
<223> OTHER INFORMATION: DLD-5

<400> SEQUENCE: 38

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Asp Asp Arg Ile Gly Met Thr Pro Leu His Leu Ala Ala Ile Gly Gly
            35                  40                  45

His Leu Glu Ile Val Glu Val Leu Leu Lys Asn Gly Ala Asp Val Asn
    50                  55                  60

Ala Asp Asp Val His Gly Arg Thr Pro Leu His Leu Ala Ala Gly Arg
65                  70                  75                  80

Gly His Leu Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Ser Ser Ser Glu Phe
        115                 120                 125

Gly Gly Gly Gly Ser Gly Gly Gly Ser Gly Gly Gly Ser Ala
    130                 135                 140

Ser Asp Leu Gly Lys Lys Leu Leu Glu Ala Ala Arg Ala Gly Gln Asp
```

```
145                 150                 155                 160
Asp Glu Val Arg Ile Leu Met Ala Asn Gly Ala Asp Val Asn Ala Leu
                165                 170                 175
Asp Thr His Gly Val Thr Pro Leu His Leu Ala Ala Trp Arg Gly His
                180                 185                 190
Leu Glu Ile Val Glu Val Leu Leu Lys Asn Gly Ala Asp Val Asn Ala
                195                 200                 205
Gly Asp Val Leu Gly Arg Thr Pro Leu His Leu Ala Ala Thr Phe Gly
            210                 215                 220
His Leu Glu Ile Val Glu Val Leu Leu Lys His Gly Ala Asp Ile Asn
225                 230                 235                 240
Ala Val Asp Thr Val Gly Val Thr Pro Leu His Leu Ala Ala Gly Gln
                245                 250                 255
Gly His Leu Glu Ile Val Glu Val Leu Leu Lys Tyr Gly Ala Asp Val
                260                 265                 270
Asn Ala Gln Asp Lys Phe Gly Lys Thr Ala Phe Asp Ile Ser Ile Asp
                275                 280                 285
Asn Gly Asn Glu Asp Leu Ala Glu Ile Leu Gln Ser Ser
            290                 295                 300

<210> SEQ ID NO 39
<211> LENGTH: 333
<212> TYPE: PRT
<213> ORGANISM: Artificial Sequence
<220> FEATURE:
<223> OTHER INFORMATION: DLD-6

<400> SEQUENCE: 39

Gly Ser Asp Leu Gly Lys Lys Leu Leu Glu Ala Ala Arg Ala Gly Gln
1               5                   10                  15
Asp Asp Glu Val Arg Ile Leu Met Ala Asn Gly Ala Asp Val Asn Ala
                20                  25                  30
Asp Asp Arg Ile Gly Met Thr Pro Leu His Leu Ala Ala Ile Gly Gly
            35                  40                  45
His Leu Glu Ile Val Glu Val Leu Leu Lys Asn Gly Ala Asp Val Asn
        50                  55                  60
Ala Asp Asp Val His Gly Arg Thr Pro Leu His Leu Ala Ala Gly Arg
65                  70                  75                  80
Gly His Leu Glu Ile Val Glu Val Leu His Gly Ala Asp Val Asn Ala
                85                  90                  95
Pro Asp Arg Trp Gly Arg Thr Pro Leu His Leu Ala Ala His His Gly
                100                 105                 110
His Leu Glu Ile Val Glu Val Leu Leu Lys Tyr Gly Ala Asp Val Asn
                115                 120                 125
Ala Gln Asp Lys Phe Gly Lys Thr Ala Phe Asp Ile Ser Ile Asp Asn
            130                 135                 140
Gly Asn Glu Asp Leu Ala Glu Ile Leu Gln Ser Ser Ser Glu Phe Gly
145                 150                 155                 160
Gly Gly Gly Ser Gly Gly Gly Ser Gly Gly Gly Ser Ala Ser
                165                 170                 175
Asp Leu Gly Lys Lys Leu Leu Glu Ala Ala Arg Ala Gly Gln Asp Asp
                180                 185                 190
Glu Val Arg Ile Leu Met Ala Asn Gly Ala Asp Val Asn Ala Lys Asp
                195                 200                 205
Thr Phe Gly Glu Thr Pro Leu His Leu Ala Ala Trp Lys Gly His Leu
```

```
           210                 215                 220
Glu Ile Val Glu Val Leu Leu Lys Tyr Gly Ala Asp Val Asn Ala Ser
225                 230                 235                 240

Asp Leu Leu Gly Arg Thr Pro Leu His Leu Ala Ala Trp Arg Gly His
                245                 250                 255

Leu Glu Ile Val Glu Val Leu Leu Lys Asn Gly Ala Asp Val Asn Ala
                    260                 265                 270

Ser Asp Thr Gly Gly Tyr Thr Pro Leu His Leu Ala Ala Ala Leu Gly
                275                 280                 285

His Leu Glu Ile Val Glu Val Leu Leu Lys His Gly Ala Asp Val Asn
            290                 295                 300

Ala Gln Asp Lys Phe Gly Lys Thr Ala Phe Asp Ile Ser Ile Asp Asn
305                 310                 315                 320

Gly Asn Glu Asp Leu Ala Glu Ile Leu Gln Ser Ser Ser
                325                 330

<210> SEQ ID NO 40
<211> LENGTH: 333
<212> TYPE: PRT
<213> ORGANISM: Artificial Sequence
<220> FEATURE:
<223> OTHER INFORMATION: DLD-7

<400> SEQUENCE: 40

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Asp Asp Arg Ile Gly Met Thr Pro Leu His Leu Ala Ala Ile Gly Gly
            35                  40                  45

His Leu Glu Ile Val Glu Val Leu Leu Lys Asn Gly Ala Asp Val Asn
    50                  55                  60

Ala Asp Asp Val His Gly Arg Thr Pro Leu His Leu Ala Ala Gly Arg
65                  70                  75                  80

Gly His Leu Glu Ile Val Glu Val Leu His Gly Ala Asp Val Asn Ala
                85                  90                  95

Pro Asp Arg Trp Gly Arg Thr Pro Leu His Leu Ala Ala His His Gly
                100                 105                 110

His Leu Glu Ile Val Glu Val Leu Leu Lys Tyr Gly Ala Asp Val Asn
            115                 120                 125

Ala Gln Asp Lys Phe Gly Lys Thr Ala Phe Asp Ile Ser Ile Asp Asn
        130                 135                 140

Gly Asn Glu Asp Leu Ala Glu Ile Leu Gln Ser Ser Ser Glu Phe Gly
145                 150                 155                 160

Gly Gly Gly Ser Gly Gly Gly Ser Gly Gly Gly Ser Gly Ser
                165                 170                 175

Asp Leu Gly Lys Lys Leu Leu Glu Ala Ala Arg Ala Gly Gln Asp Asp
                180                 185                 190

Glu Val Arg Ile Leu Met Ala Asn Gly Ala Asp Val Asn Ala Val Asp
            195                 200                 205

Arg Ala Gly Thr Thr Pro Leu His Leu Ala Ala His Gly Gly His Leu
        210                 215                 220

Glu Ile Val Glu Val Leu Leu Lys Tyr Gly Ala Asp Val Asn Ala Arg
225                 230                 235                 240

Asp Leu Leu Gly Arg Thr Pro Leu His Leu Ala Ala Trp Arg Gly His
```

```
                    245                 250                 255
Leu Glu Ile Val Glu Val Leu Lys His Gly Ala Asp Val Asn Ala
            260                 265                 270

Ser Asp Pro Leu Gly Ile Thr Pro Leu His Leu Ala Ala Thr Gly
        275                 280                 285

His Leu Glu Ile Val Glu Val Leu Leu Lys Asn Gly Ala Asp Val Asn
    290                 295                 300

Ala Gln Asp Lys Phe Gly Lys Thr Ala Phe Asp Ile Ser Ile Asp Asn
305                 310                 315                 320

Gly Asn Glu Asp Leu Ala Glu Ile Leu Gln Ser Ser Ser
                325                 330

<210> SEQ ID NO 41
<211> LENGTH: 333
<212> TYPE: PRT
<213> ORGANISM: Artificial Sequence
<220> FEATURE:
<223> OTHER INFORMATION: DLD-10

<400> SEQUENCE: 41

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asp Asp Arg Ile Gly Met Thr Pro Leu His Leu Ala Ala Ile Gly Gly
        35                  40                  45

His Leu Glu Ile Val Glu Val Leu Leu Lys Asn Gly Ala Asp Val Asn
    50                  55                  60

Ala Asp Asp Val His Gly Arg Thr Pro Leu His Leu Ala Ala Gly Arg
65                  70                  75                  80

Gly His Leu Glu Ile Val Glu Val Leu His Gly Ala Asp Val Asn Ala
                85                  90                  95

Pro Asp Arg Trp Gly Arg Thr Pro Leu His Leu Ala Ala His His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Ser Ser Ser Glu Phe Gly
145                 150                 155                 160

Gly Gly Gly Ser Gly Gly Gly Ser Gly Gly Gly Ser Gly Ser
                165                 170                 175

Asp Leu Gly Lys Lys Leu Leu Glu Ala Ala Arg Ala Gly Gln Asp Asp
            180                 185                 190

Glu Val Arg Ile Leu Met Ala Asn Gly Ala Asp Val Asn Ala Leu Asp
        195                 200                 205

Thr His Gly Val Thr Pro Leu His Leu Ala Ala Trp Arg Gly His Leu
    210                 215                 220

Glu Ile Val Glu Val Leu Leu Lys Asn Gly Ala Asp Val Asn Ala Gly
225                 230                 235                 240

Asp Val Leu Gly Arg Thr Pro Leu His Leu Ala Ala Thr Phe Gly His
                245                 250                 255

Leu Glu Ile Val Glu Val Leu Leu Lys His Gly Ala Asp Ile Asn Ala
            260                 265                 270

Val Asp Thr Val Gly Val Thr Pro Leu His Leu Ala Ala Gly Gln Gly
```

```
        275                 280                 285
His Leu Glu Ile Val Glu Val Leu Lys Tyr Gly Ala Asp Val Asn
    290                 295                 300

Ala Gln Asp Lys Phe Gly Lys Thr Ala Phe Asp Ile Ser Ile Asp Asn
305                 310                 315                 320

Gly Asn Glu Asp Leu Ala Glu Ile Leu Gln Ser Ser Ser
                325                 330
```

<210> SEQ ID NO 42
<211> LENGTH: 333
<212> TYPE: PRT
<213> ORGANISM: Artificial Sequence
<220> FEATURE:
<223> OTHER INFORMATION: DLD-11

<400> SEQUENCE: 42

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Asp Asp Arg Ile Gly Met Thr Pro Leu His Leu Ala Ala Ile Gly Gly
            35                  40                  45

His Leu Glu Ile Val Glu Val Leu Leu Lys Asn Gly Ala Asp Val Asn
    50                  55                  60

Ala Asp Asp Val His Gly Arg Thr Pro Leu His Leu Ala Ala Gly Arg
65                  70                  75                  80

Gly His Leu Glu Ile Val Glu Val Leu His Gly Ala Asp Val Asn Ala
                85                  90                  95

Pro Asp Arg Trp Gly Arg Thr Pro Leu His Leu Ala Ala His His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Ser Ser Ser Glu Phe Gly
145                 150                 155                 160

Gly Gly Gly Ser Gly Gly Gly Ser Gly Gly Gly Ser Ala Ser
                165                 170                 175

Asp Leu Gly Lys Lys Leu Leu Glu Ala Ala Arg Ala Gly Gln Asp Asp
            180                 185                 190

Glu Val Arg Ile Leu Met Ala Asn Gly Ala Asp Val Asn Ala Tyr Asp
        195                 200                 205

Ala Arg Gly Val Thr Pro Leu His Leu Ala Ala Phe Ser Gly His Leu
    210                 215                 220

Glu Ile Val Glu Val Leu Leu Lys Asn Gly Ala Asp Val Asn Ala Ile
225                 230                 235                 240

Asp Val Ile Gly Met Thr Pro Leu His Leu Ala Ala Trp Ile Gly His
                245                 250                 255

Leu Glu Ile Val Glu Val Leu Leu Lys His Gly Ala Asp Val Asn Ala
            260                 265                 270

Val Asp Arg Ser Gly Asn Thr Pro Leu His Leu Ala Ala Trp Leu Gly
        275                 280                 285

His Leu Glu Ile Val Glu Val Leu Leu Lys Tyr Gly Ala Asp Val Asn
    290                 295                 300

Ala Gln Asp Lys Phe Gly Lys Thr Ala Phe Asp Ile Ser Ile Asp Asn
```

Gly Asn Glu Asp Leu Ala Glu Ile Leu Gln Ser Ser Ser
         325                 330

<210> SEQ ID NO 43
<211> LENGTH: 333
<212> TYPE: PRT
<213> ORGANISM: Artificial Sequence
<220> FEATURE:
<223> OTHER INFORMATION: DLD-12

<400> SEQUENCE: 43

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Asp Asp Arg Ile Gly Met Thr Pro Leu His Leu Ala Ala Ile Gly Gly
        35                  40                  45

His Leu Glu Ile Val Glu Val Leu Leu Lys Asn Gly Ala Asp Val Asn
    50                  55                  60

Ala Asp Asp Val His Gly Arg Thr Pro Leu His Leu Ala Ala Gly Arg
65                  70                  75                  80

Gly His Leu Glu Ile Val Glu Val Leu His Gly Ala Asp Val Asn Ala
                85                  90                  95

Pro Asp Arg Trp Gly Arg Thr Pro Leu His Leu Ala Ala His His Gly
            100                 105                 110

His Leu Glu Ile Val Glu Val Leu Leu Lys Tyr Gly Ala Asp Val Asn
        115                 120                 125

Ala Gln Asp Lys Phe Gly Lys Thr Ala Phe Asp Ile Ser Ile Asp Asn
130                 135                 140

Gly Asn Glu Asp Leu Ala Glu Ile Leu Gln Ser Ser Ser Glu Phe Gly
145                 150                 155                 160

Gly Gly Gly Ser Gly Gly Gly Ser Gly Gly Gly Ser Ala Ser
                165                 170                 175

Asp Leu Gly Lys Lys Leu Leu Glu Ala Ala Arg Ala Gly Gln Asp Asp
            180                 185                 190

Glu Val Arg Ile Leu Met Ala Asn Gly Ala Asp Val Asn Ala Thr Asp
        195                 200                 205

His Leu Gly Val Thr Pro Leu His Leu Ala Ala Val Leu Gly His Leu
    210                 215                 220

Glu Ile Val Glu Val Leu Leu Lys His Gly Ala Asp Val Asn Ala Tyr
225                 230                 235                 240

Asp Ile Leu Gly Arg Thr Pro Leu His Leu Ala Ala Trp Arg Gly His
                245                 250                 255

Leu Glu Ile Val Glu Val Leu Leu Lys Tyr Gly Ala Asp Val Asn Ala
            260                 265                 270

Val Asp Thr Met Gly Glu Thr Pro Leu His Leu Ala Ala Gly Met Gly
        275                 280                 285

His Leu Glu Ile Val Glu Val Leu Leu Lys His Gly Ala Asp Val Asn
    290                 295                 300

Ala Gln Asp Lys Phe Gly Lys Thr Ala Phe Asp Ile Ser Ile Asp Asn
305                 310                 315                 320

Gly Asn Glu Asp Leu Ala Glu Ile Leu Gln Ser Ser Ser
                325                 330

<210> SEQ ID NO 44
<211> LENGTH: 28
<212> TYPE: DNA
<213> ORGANISM: Artificial Sequence
<220> FEATURE:
<223> OTHER INFORMATION: Ran2-D-F

<400> SEQUENCE: 44
catgtgcatt atctgggatc cgacctgg                                    28

<210> SEQ ID NO 45
<211> LENGTH: 23
<212> TYPE: DNA
<213> ORGANISM: Artificial Sequence
<220> FEATURE:
<223> OTHER INFORMATION: Ran2-D-R

<400> SEQUENCE: 45
taacaggccg caagctttta cga                                         23

<210> SEQ ID NO 46
<211> LENGTH: 64
<212> TYPE: DNA
<213> ORGANISM: Artificial Sequence
<220> FEATURE:
<223> OTHER INFORMATION: Linker-BSAi-D-F

<400> SEQUENCE: 46
ttagctggtc tctggaggga gcggaggcgg agggagcgct agcgacctgg gtaagaaact   60
gctg                                                              64

<210> SEQ ID NO 47
<211> LENGTH: 65
<212> TYPE: DNA
<213> ORGANISM: Artificial Sequence
<220> FEATURE:
<223> OTHER INFORMATION: Linker-BSAi-D-R

<400> SEQUENCE: 47
gaaatcctgc aatcgagctc ggaattcgga ggcggaggga gcggaggcgg agtgagacct   60
tagct                                                             65

<210> SEQ ID NO 48
<211> LENGTH: 15
<212> TYPE: PRT
<213> ORGANISM: Artificial Sequence
<220> FEATURE:
<223> OTHER INFORMATION: (GGGGS)x3 Linker

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 331
<212> TYPE: PRT
<213> ORGANISM: Artificial Sequence
<220> FEATURE:
<223> OTHER INFORMATION: U3D16

<400> SEQUENCE: 49

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

```
Asp Asp Arg Ile Gly Met Thr Pro Leu His Leu Ala Ala Ile Gly Gly
         35              40              45

His Leu Glu Ile Val Glu Val Leu Leu Lys Asn Gly Ala Asp Val Asn
     50              55              60

Ala Asp Asp Val His Gly Arg Thr Pro Leu His Leu Ala Ala Gly Arg
 65              70              75              80

Gly His Leu Glu Ile Val Glu Val Leu His Gly Ala Asp Val Asn Ala
             85              90              95

Pro Asp Arg Trp Gly Arg Thr Pro Leu His Leu Ala Ala His His Gly
             100             105             110

His Leu Glu Ile Val Glu Val Leu Leu Lys Tyr Gly Ala Asp Val Asn
     115             120             125

Ala Gln Asp Lys Phe Gly Lys Thr Ala Phe Asp Ile Ser Ile Asp Ser
     130             135             140

Gly Asn Glu Asp Leu Ala Glu Ile Leu Gln Ser Ser Ser Gly Gly Gly
 145             150             155             160

Gly Ser Gly Gly Gly Gly Ser Gly Gly Gly Gly Ser Gly Ser Asp Leu
             165             170             175

Gly Lys Lys Leu Leu Glu Ala Ala Arg Ala Gly Gln Asp Asp Glu Val
             180             185             190

Arg Ile Leu Met Ala Asn Gly Ala Asp Val Asn Ala Ala Asp Arg Tyr
             195             200             205

Gly Pro Thr Pro Leu His Leu Ala Ala Tyr Arg Gly His Leu Glu Ile
             210             215             220

Val Glu Val Leu Leu Lys His Gly Ala Asp Val Asn Ala Lys Asp Val
 225             230             235             240

Leu Gly Trp Thr Pro Leu His Leu Ala Ala Trp Ile Gly His Leu Glu
             245             250             255

Ile Val Glu Val Leu Leu Lys Asn Gly Ala Asp Val Asn Ala Arg Asp
             260             265             270

Arg Thr Gly Glu Thr Pro Leu His Leu Ala Ala Ile Gly His Leu
     275             280             285

Glu Ile Val Glu Val Leu Leu Lys Asn Gly Ala Asp Val Asn Ala Gln
     290             295             300

Asp Lys Phe Gly Lys Thr Ala Phe Asp Ile Ser Ile Asp Asn Gly Asn
305             310             315             320

Glu Asp Leu Ala Glu Ile Leu Gln Ser Ser Ser
             325             330
```